United States Patent
Usmani et al.

(10) Patent No.: US 10,697,024 B2
(45) Date of Patent: Jun. 30, 2020

(54) METHODS OF DETERMINING IMIDS RESISTANCE IN PLASMA CELL DISORDERS

(71) Applicant: The Charlotte Mecklenburg Hospital Authority, Charlotte, NC (US)

(72) Inventors: Saad Z. Usmani, Charlotte, NC (US); Qing Zhang, Charlotte, NC (US); Manisha Bhutani, Charlotte, NC (US)

(73) Assignee: The Charlotte-Mecklenburg Hospital Authority, Charlotte, NC (US)

( * ) Notice: Subject to any disclaimer, the term of this patent is extended or adjusted under 35 U.S.C. 154(b) by 85 days.

(21) Appl. No.: 15/821,286

(22) Filed: Nov. 22, 2017

(65) Prior Publication Data
US 2018/0148796 A1    May 31, 2018

Related U.S. Application Data

(60) Provisional application No. 62/425,787, filed on Nov. 23, 2016.

(51) Int. Cl.
| | |
|---|---|
| *C12Q 1/6886* | (2018.01) |
| *A61K 31/00* | (2006.01) |
| *A61K 39/00* | (2006.01) |

(52) U.S. Cl.
CPC .......... *C12Q 1/6886* (2013.01); *A61K 31/00* (2013.01); *A61K 39/00* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

FOREIGN PATENT DOCUMENTS

WO    WO 2015/144929    * 10/2015

OTHER PUBLICATIONS

Whitehead (Genome Biology 2005 vol. 6 Issue 2 Article R13).*
Chan (G&P magazine 2006 vol. 6 No. 3 pp. 20-26).*
Coleman (Drug Discovery Today. 2003. 8: 233-235).*
Agarwal et al. "Practical Considerations in Managing Relapsed Multiple Myeloma" Clinical Lymphoma, Myeloma & Leukemia, 17(2):69-77 (2017) (Abstract only).
Atrash et al. "Cardiac complications in relapsed and refractory multiple myeloma patients treated with carfilzomib" Blood Cancer Journal, 5(1):e272 (2015).
Barlogie et al. "Thalidomide and Hematopoietic-Cell Transplantation for Multiple Myeloma" The New England Journal of Medicine, 354(10):1021-1030 (2006).
Barlogie et al. "Incorporating bortezomib into upfront treatment for multiple myeloma: early results of total therapy 3" British Journal of Haematology, 138(2):176-185 (2007).
Bhutani et al. "Bone marrow abnormalities and early bone lesions in multiple myeloma and its precursor disease: A prospective study using functional and morphologic imaging" Leukemia & Lymphoma, 57(5):1114-1121 (2016).
Bhutani et al. "Cutaneous manifestations of multiple myeloma and other plasma cell proliferative disorders" Seminars in Oncology, 43(3):395-400 (2016) (Abstract only).
Bhutani et al. "Investigation of a gene signature to predict response to immunomodulatory derivatives for patients with multiple myeloma: an exploratory, retrospective study using microarray datasets from prospective clinical trials" The Lancet Haematology, 4:e443-451 (2017).
Burington et al. "Tumor Cell Gene Expression Changes Following Short-term in vivo Exposure to Single Agent Chemotherapeutics are Related to Survival in Multiple Myeloma" Clinical Cancer Research, 14(15):4821-4829 (2008).
Chang et al. "Mechanism of immunomodulatory drugs' action in the treatment of multiple myeloma" Acta Biochimica et Biophysica Sinica, 46(3):240-253 (2014).
Decaux et al. "Prediction of Survival in Multiple Myeloma Based on Gene Expression Profiles Reveals Cell Cycle and Chromosomal Instability Signatures in High-Risk Patients and Hyperdiploid Signatures in Low-Risk Patients: A Study of the Intergroupe Francophone du Myelome" Journal of Clinical Oncology, 26(29):4798-4805 (2008).
Dickmanns et al. "Structural Basis of Targeting the Exportin CRM1 in Cancer" Cells, 4:538-568 (2015).
Friend et al. "Clinical potential of SLAMF7 antibodies—focus on elotuzumab in multiple myeloma" Drug Design, Development and Therapy, 11:893-900 (2017).
Heuck et al. "Five gene probes carry most of the discriminatory power of the 70-gene risk model in multiple myeloma" Leukemia, 28:2410-2413 (2014).
Ito et al. "Identification of a Primary Target of Thalidomide Teratogenicity" Science, 327(5971):1345-1350 (2010).
Kau et al. "Nuclear transport and cancer: from mechanism to intervention" Nature Reviews Cancer, 4:106-117 (2004) (Abstract only).
Kronke et al. "Lenalidomide Causes Selective Degradation of IKZF1 and IKZF3 in Multiple Myeloma Cells" Science, 343(6168):301-305 (2014).
Kronke et al. "IKZF1 expression is a prognostic marker in newly diagnosed standard-risk multiple myeloma treated with lenalidomide and intensive chemotherapy: a study of the German Myeloma Study Group (DSMM)" Leukemia, 31 (6):1363-1367 (2017) (Abstract only).
Kuiper et al. "A gene expression signature for high-risk multiple myeloma" Leukemia, 26(11):2406-2413 (2012) (Abstract only).
Lu et al. "The Myeloma Drug Lenalidomide Promotes the Cereblon-Dependent Destruction of Ikaros Proteins" Science, 343(6168):305-309 (2014).
Nair et al. "Superior results of Total Therapy 3 (2003-33) in gene expression profiling—defined low-risk multiple myeloma confirmed in subsequent trial 2006-66 with VRD maintenance" Blood, 115(21):4168-4173 (2010).

(Continued)

*Primary Examiner* — Amanda Haney
(74) *Attorney, Agent, or Firm* — Myers Bigel, P.A.

(57) ABSTRACT

The present invention provides methods for determining immunomodulatory derivatives (IMiDs) resistance in a subject having a plasma cell disorder.

8 Claims, 16 Drawing Sheets

(56) References Cited

OTHER PUBLICATIONS

Neubert et al. "Thalidomide derivatives and the immune system. I. Changes in the pattern of integrin receptors and other surface markers on T lymphocyte subpopulations of marmoset blood" Archives of Toxicology, 67(1):1-17 (1993).

Pan et al. "NFAT Gene Family in Inflammation and Cancer" Current Molecular Medicine, 13(4):543-554 (2013).

Sehgal et al. "Clinical and pharmacodynamic analysis of pomalidomide dosing strategies in myeloma: impact of immune activation and cereblon targets" Blood, 125:4042-4051 (2015).

Senapedis et al. "Clinical translation of nuclear export inhibitors in cancer" Seminars in Cancer Biology, 27:74-86 (2014) (Abstract only).

Shaughnessy et al. "A validated gene expression model of high-risk multiple myeloma is defined by deregulated expression of genes mapping to chromosome 1" Blood, 109:2276-2284 (2007).

Sonneveld et al. "Bortezomib Induction and Maintenance Treatment in Patients With Newly Diagnosed Multiple Myeloma: Results of the Randomized Phase III HOVON-65/GMMG-HD4 Trial" Journal of Clinical Oncology, 30 (24):2946-2955 (2012).

Usmani et al. "Phase II study of pomalidomide in high-risk relapsed and refractory multiple myeloma" Leukemia, 28:2413-2415 (2014).

Usmani et al. "Analyses of Real World Data on Overall Survival in Multiple Myeloma Patients with at Least 3 Prior Lines of Therapy Including a PI and an IMiD, or Double Refractory to a PI and an IMiD" (2 pages) 57th Annual Meeting & Exposition, Orlando, Florida Dec. 5-8, 2015.

Usmani et al. "Defining and treating high-risk multiple myeloma" Leukemia, 29(11):2119-2125 (2015) (Abstract only).

Vogl et al. "Selinexor and Low Dose Dexamethasone (Sd) in Patients with Lenalidomide, Pomalidomide, Bortezomib, Carfilzomib and Anti-CD38 Ab Refractory Multiple Myeloma (MM): STORM Study" Blood, 128(22):491 (2016) (Abstract only).

Zhou et al. "Prediction of cytogenetic abnormalities with gene expression profiles" Blood, 119(21):e148-e150 (2012).

Zhu et al. "Identification of cereblon-binding proteins and relationship with response and survival after IMiDs in multiple myeloma" Blood, 124(4):536-545 (2014).

Bhutani et al. Multiple Myeloma: Is It Time for Biomarker-Driven Therapy? *American Society of Clinical Oncology Educational Book* e493-503 (2015).

Bhutani et al. "Investigation of a gene signature to predict response to immunomodulatory derivatives for patients with multiple myeloma: an exploratory, retrospective study using microarray datasets from prospective clinical trials" *The Lancet Haematology* 4(9):e443-e451 (2017) (Abstract Only).

Durie et al. "International uniform response criteria for multiple myeloma" *Leukemia* 20:1467-1473 (2006).

Hubbell et al. "Robust estimators for expression analysis" *Bioinformatics* 18(12):1585-1592 (2002).

Irizarry et al. "Exploration, normalization, and summaries of high density oligonucleotide array probe level data" *Biostatistics* 4(2):249-264 (2003).

Li et al. "Model-based analysis of oligonucleotide arrays: Expression index computation and outlier detection" *Proceedings of the National Academy of Sciences* 98(1):31-36 (2001).

Li et al. "Model-based analysis of oligonucleotide arrays: model validation, design issues and standard error application" *Genome Biology* 2(8):0032-1-0032-11 (2001).

Rajkumar et al. "Consensus recommendations for the uniform reporting of clinical trials: report of the International Myeloma Workshop Consensus Panel 1" *Blood* 117(18):4691-4695 (2011).

Shaughnessy et al. "Pharmacogenomics of bortezomib test-dosing identifies hyperexpression of proteasome genes, especially PSMD4, as novel high-risk feature in myeloma treated with Total Therapy 3" *Blood* 118(13):3512-3524 (2011).

Wu et al. "A Model Based Background Adjustment for Oligonucleotide Expression Arrays" *Johns Hopkins University, Dept. of Biostatistics Working Papers* Paper 1, pp. 1-26 (2004).

Zhan et al. "The molecular classification of multiple myeloma" *Blood* 108:2020-2028 (2006).

\* cited by examiner

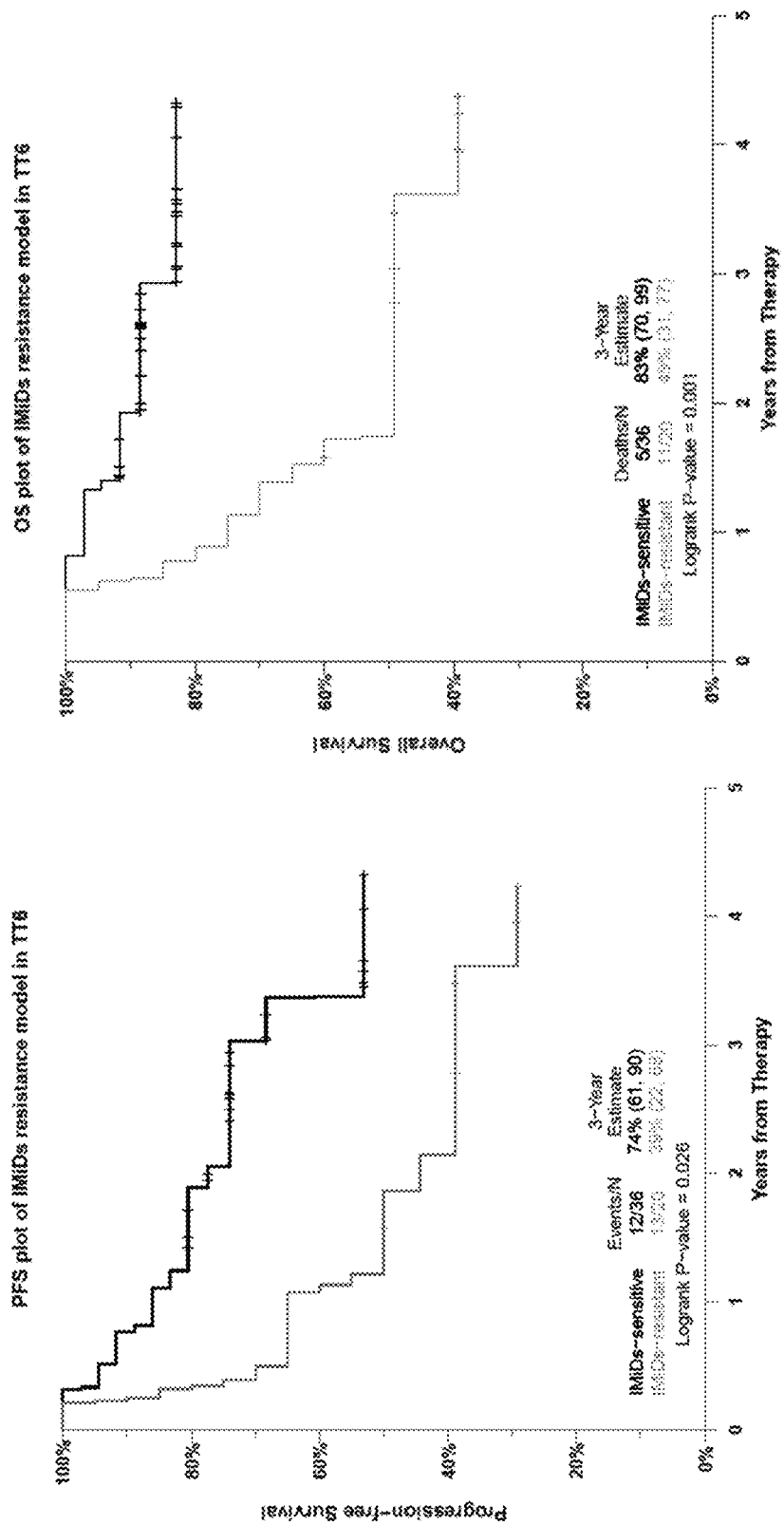

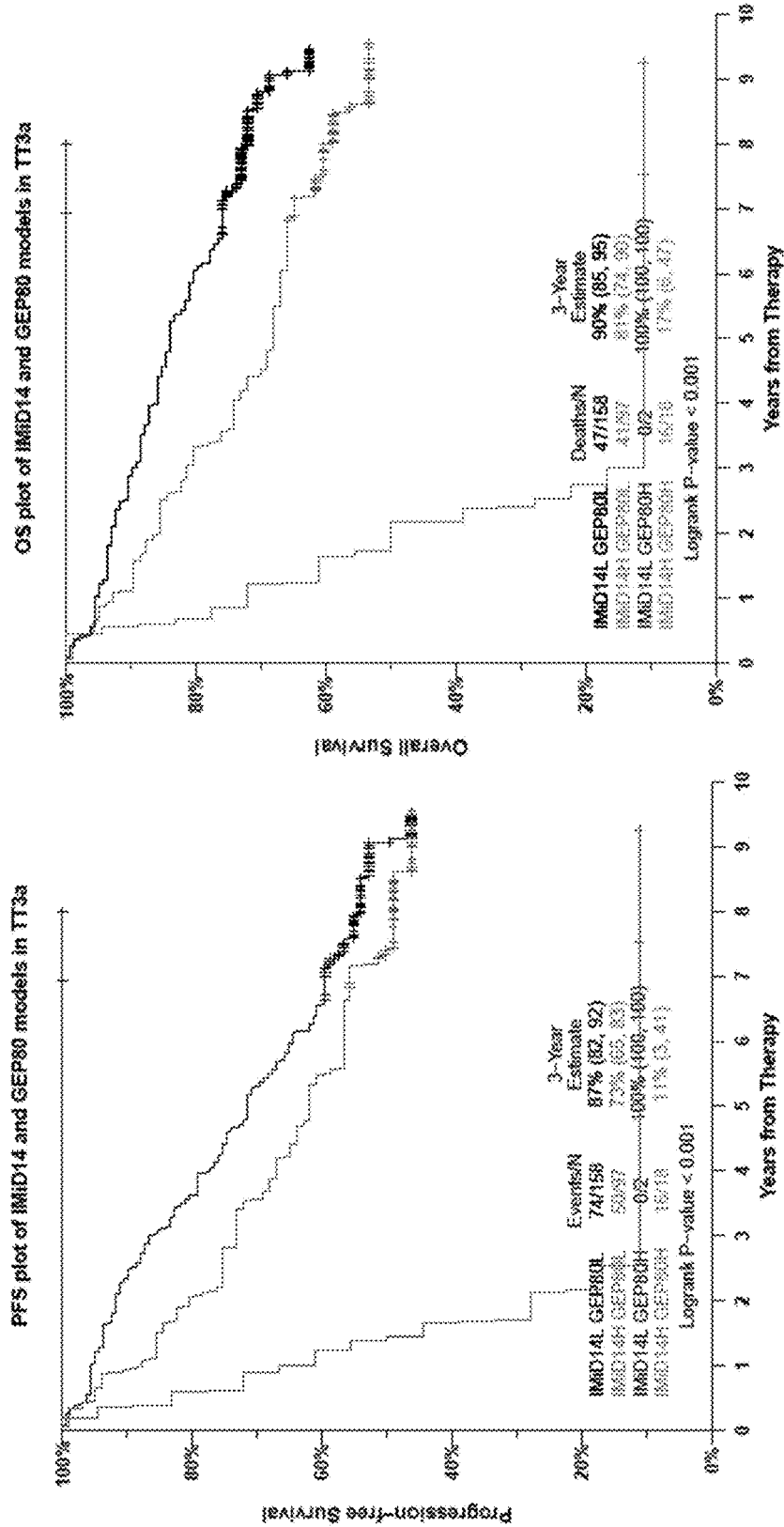

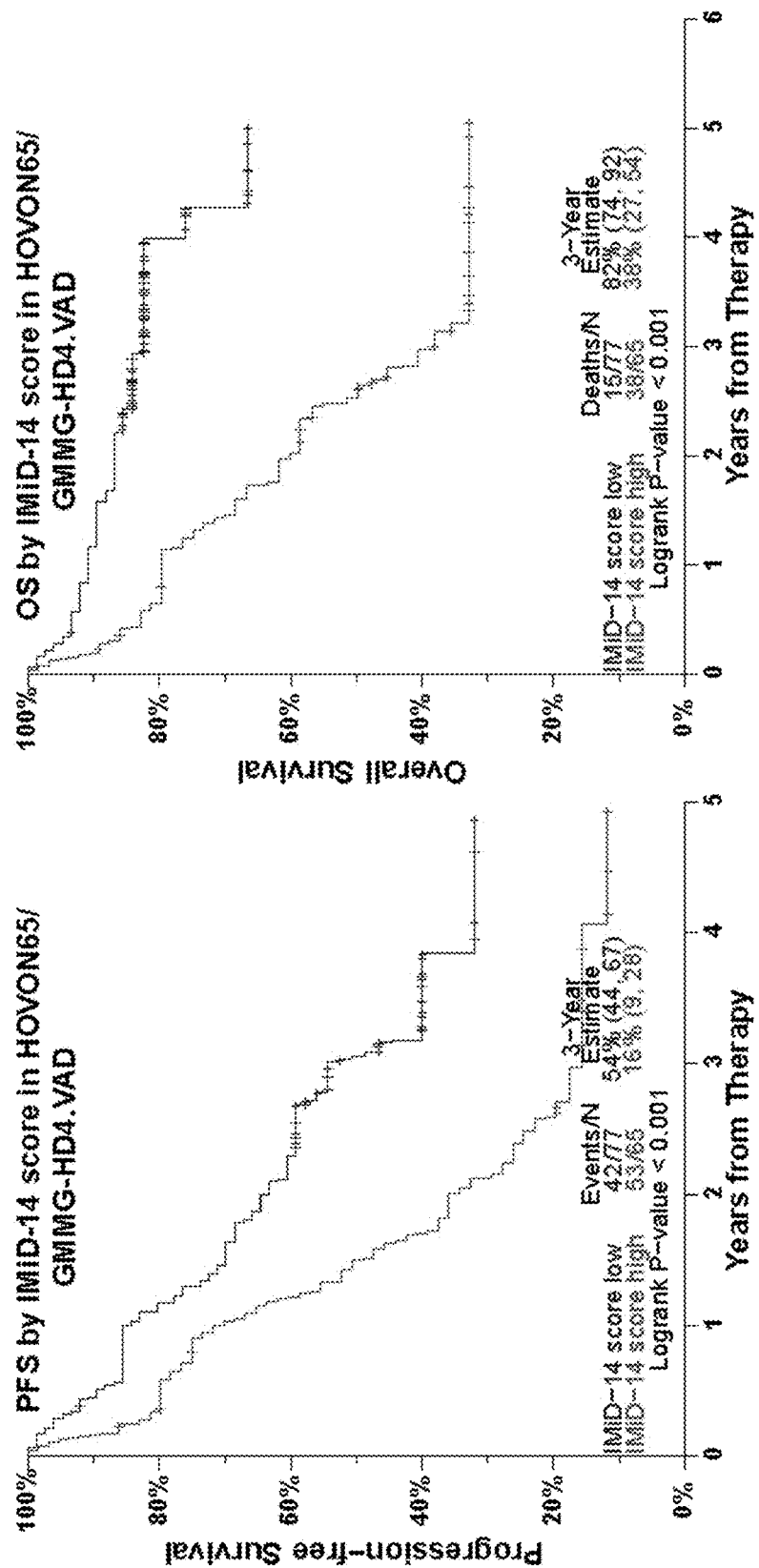

METHODS OF DETERMINING IMIDS RESISTANCE IN PLASMA CELL DISORDERS

STATEMENT OF PRIORITY

This application claims the benefit, under 35 U.S.C. § 119(e), of U.S. Provisional Application Ser. No. 62/425,787, filed Nov. 23, 2016, the entire contents of which are incorporated by reference herein.

RESERVATION OF COPYRIGHT

A portion of the disclosure of this patent document contains material which is subject to copyright protection. The copyright owner, The Charlotte-Mecklenburg Hospital Authority, doing business as "Carolinas HealthCare System," Charlotte, N.C., has no objection to the reproduction by anyone of the patent document or the patent disclosure, as it appears in the U.S. Patent and Trademark Office patent file or records, but otherwise reserves all copyright rights whatsoever.

FIELD OF THE INVENTION

The present invention relates to methods for determining immunomodulatory derivatives (IMiDs) resistance in a subject with a plasma cell disorder.

BACKGROUND OF THE INVENTION

Immunomodulatory derivatives (IMiDs), such as thalidomide, lenalidomide and pomalidomide have become an integral part of multiple myeloma (MM) treatment. Initially approved for relapsed/refractory setting, and later introduced into the upfront setting with and without transplant, IMiD based treatment combinations have produced unprecedented rates of disease response and progression free survival (PFS) benefit. Despite these therapeutic advances, the success of long-term treatment with IMiDs is limited by disease relapse and progression that occur almost universally at least due to innate or acquired drug resistance.

The precise mechanisms of IMiDs resistance are not entirely clear. Recently, it was shown that lenalidomide (Len) and other agents in the class of IMiDs mediate anti-myeloma effects through E3 ubiquitin ligase-cereblon to increase degradation of transcription factors Ikaros and Aiolos. However, attempts to accurately predict resistance based on expression level of individual predictive markers such as cereblon over-expression or deregulation of its downstream target IRF4 show contradictory results in different studies.

Several gene-expression profiling (GEP) signatures have been developed to stratify MM patients into different risk groups based on GEP samples from different clinical trials. These prognostic signatures are either focused on bortezomib (Bor) response genes or are more general to multiple agent chemotherapies used in the corresponding trials, but none of them are IMiDs specific. Recent studies on large-scale analysis of gene expression in MM have underscored the considerable potential of this strategy to elucidate resistance/response signature associated with IMiDs.

While the discovery of cereblon as a target of IMiDs has led to a better understanding of the molecular mechanism of action by these agents, the prognostic value of cereblon, Ikaros, or Aiolos is controversial. It has been previously shown that lenalidomide, and other agents in this class of IMiDs act through cereblon to increase the degradation of Ikaros and Aiolos transcription factors. However, low expression of cereblon, Ikaros and Aiolos in TT2 (thalidomide arm) and TT3a patients does not predict shorter PFS or overall survival (OS). Thus, there remains a need for improved methods for predicting resistance and/or response of MM to IMiDs treatment.

The present invention overcomes previous shortcomings in the art by providing methods for identifying IMiDs resistance in a subject.

SUMMARY OF THE INVENTION

The present invention is related to the development of a method based on a gene expression profile/signature that has the ability to determine resistance to IMiDs treatment and outcome in subjects having a plasma cell disorder, and in particular embodiments, multiple myeloma (MM) patients. Clinical and pharmacogenomic data were combined from MM patients who underwent IMiDs-based therapies, and genes related to IMiDs response were identified. An IMiDs-resistance gene profile/signature, IMiD-14, was built from these data. No other molecular signature has been reported that can identify resistance to IMiDs class of drugs. On the basis of this gene signature, MM patients can be classified as either sensitive (low score) or resistant (high score) to IMiDs. This score system exhibited robustness in stratifying patients in four independent clinical studies in which patients were treated with IMiD-based regimens. Patients with a high IMiD-14 score in all the studies exhibited poor PFS and OS compared with patients who had a low IMiD-14 score.

Thus, in an aspect of the invention, provided is a method for identifying whether a patient having a plasma cell disorder, such as an MM patient, has, or is at risk for having IMiDs resistance, including: obtaining a biological sample from the patient; measuring on a platform gene expression levels of prognosis-favorable genes for IMiDs response and gene expression levels for prognosis-unfavorable genes for IMiDs response in the sample; normalizing the gene expression level of prognosis-favorable genes for IMiDs response to obtain a normalized gene expression level for prognosis-favorable genes for IMiDs response and normalizing the gene expression level of prognosis-unfavorable genes IMiDs response to obtain a normalized gene expression level for prognosis-unfavorable genes IMiDs response; obtaining a difference between the normalized gene expression level for prognosis-favorable genes for IMiDs response and the normalized gene expression level for prognosis-unfavorable genes IMiDs response to provide a gene expression profile or signature; and comparing the gene expression profile or signature to a pre-defined threshold or cut-off value, wherein if the gene expression profile or signature exceeds the threshold or cut-off value, the gene expression profile is indicative that the patient has, or is at risk for having IMiDs resistance.

In another aspect of the invention, provided is a method for identifying whether a patient having a plasma cell disorder, such as an MM patient, is developing, or is at risk for developing IMiDs resistance, including: obtaining a biological sample from the patient; measuring on a platform gene expression levels of prognosis-favorable genes for IMiDs response and gene expression levels for prognosis-unfavorable genes for IMiDs response in the sample; normalizing the gene expression level of prognosis-favorable genes for IMiDs response to obtain a normalized gene expression level for prognosis-favorable genes for IMiDs response and normalizing the gene expression level of prognosis-unfavorable genes IMiDs response to obtain a normalized gene expression level for prognosis-unfavorable genes IMiDs response; obtaining a difference between the normalized gene expression level for prognosis-favorable genes for IMiDs response and the normalized gene expression level for prognosis-unfavorable genes IMiDs response to provide a gene expression profile or signature; and comparing the gene expression profile to a pre-defined threshold or cut-off value, wherein if the gene expression profile exceeds the threshold or cut-off value, the gene expression profile is indicative that the patient is developing, or is at risk for developing IMiDs resistance.

In an additional aspect of the invention, provided is a method of identifying a patient having a plasma cell disorder, such as an MM patient, having a poor prognosis for IMiDs treatment, including: obtaining a biological sample from the patient; measuring on a platform gene expression levels of prognosis-favorable genes for IMiDs response and gene expression levels for prognosis-unfavorable genes for IMiDs response in the sample; normalizing the gene expression level of prognosis-favorable genes for IMiDs response to obtain a normalized gene expression level for prognosis-favorable genes for IMiDs response and normalizing the gene expression level of prognosis-unfavorable genes IMiDs response to obtain a normalized gene expression level for prognosis-unfavorable genes IMiDs response; obtaining a difference between the normalized gene expression level for prognosis-favorable genes for IMiDs response and the normalized gene expression level for prognosis-unfavorable genes IMiDs response to provide a gene expression profile or signature; and comparing the gene expression profile to a pre-defined threshold or cut-off value, wherein if the gene expression profile exceeds the threshold or cut-off value, the gene expression profile is indicative that the patient has a poor prognosis for IMiDs treatment.

In another aspect of this invention, provided is a method of monitoring response to IMiDs treatment of a patient having a plasma cell disorder, such as an MM patient, for IMiDs resistance, including: obtaining a biological sample from the patient; measuring on a platform gene expression levels of prognosis-favorable genes for IMiDs response and gene expression levels for prognosis-unfavorable genes for IMiDs response in the sample; normalizing the gene expression level of prognosis-favorable genes for IMiDs response to obtain a normalized gene expression level for prognosis-favorable genes for IMiDs response and normalizing the gene expression level of prognosis-unfavorable genes IMiDs response to obtain a normalized gene expression level for prognosis-unfavorable genes IMiDs response; obtaining a difference between the normalized gene expression level for prognosis-favorable genes for IMiDs response and the normalized gene expression level for prognosis-unfavorable genes IMiDs response to provide a gene expression profile or signature; and comparing the gene expression profile to a pre-defined threshold or cut-off value, wherein if the gene expression profile exceeds the threshold or cut-off value, the gene expression profile is indicative that the patient will not respond to IMiDs treatment.

The present invention is explained in greater detail in the drawings herein and the specification set forth below. The disclosures of all patents, patent publications, non-patent references and accession numbers cited herein are incorporated by reference herein in their entirety.

BRIEF DESCRIPTION OF THE DRAWINGS

FIGS. 5A and 5B: Validation cohort TT6 (pretreated M patients, induction with VTD-PACE and maintenance with VRD or VMD for 3 years). K-M estimates in IMiD-14 high score (gray) and IMiD-14 low score (black) showed inferior 3-year PFS (A) (39% vs. 74%, P=0.026) and OS (B) (49% vs. 83%, P=0.001).

FIGS. 8A and 8B: (A) PFS plot of IMiD14 and GEP80 models in TT3a. (B) OS plot of IMiD14 and GEP80 models in TT3a.

FIGS. 11A and 11B: IMiD-14 model of MM patients treated with polychemotherapy including an IMiD. The IMiD-14 model divided MM patients who were treated with polychemotherapy including IMiDs into two subgroups with significantly different PFS and OS. (A) HOVON65/GMMG-HD4 VAD arm validation set PFS curve. (B) HOVON65/GMMG-HD4 VAD arm validation set OS curve.

DETAILED DESCRIPTION OF THE INVENTION

Figures 1A, 1B:
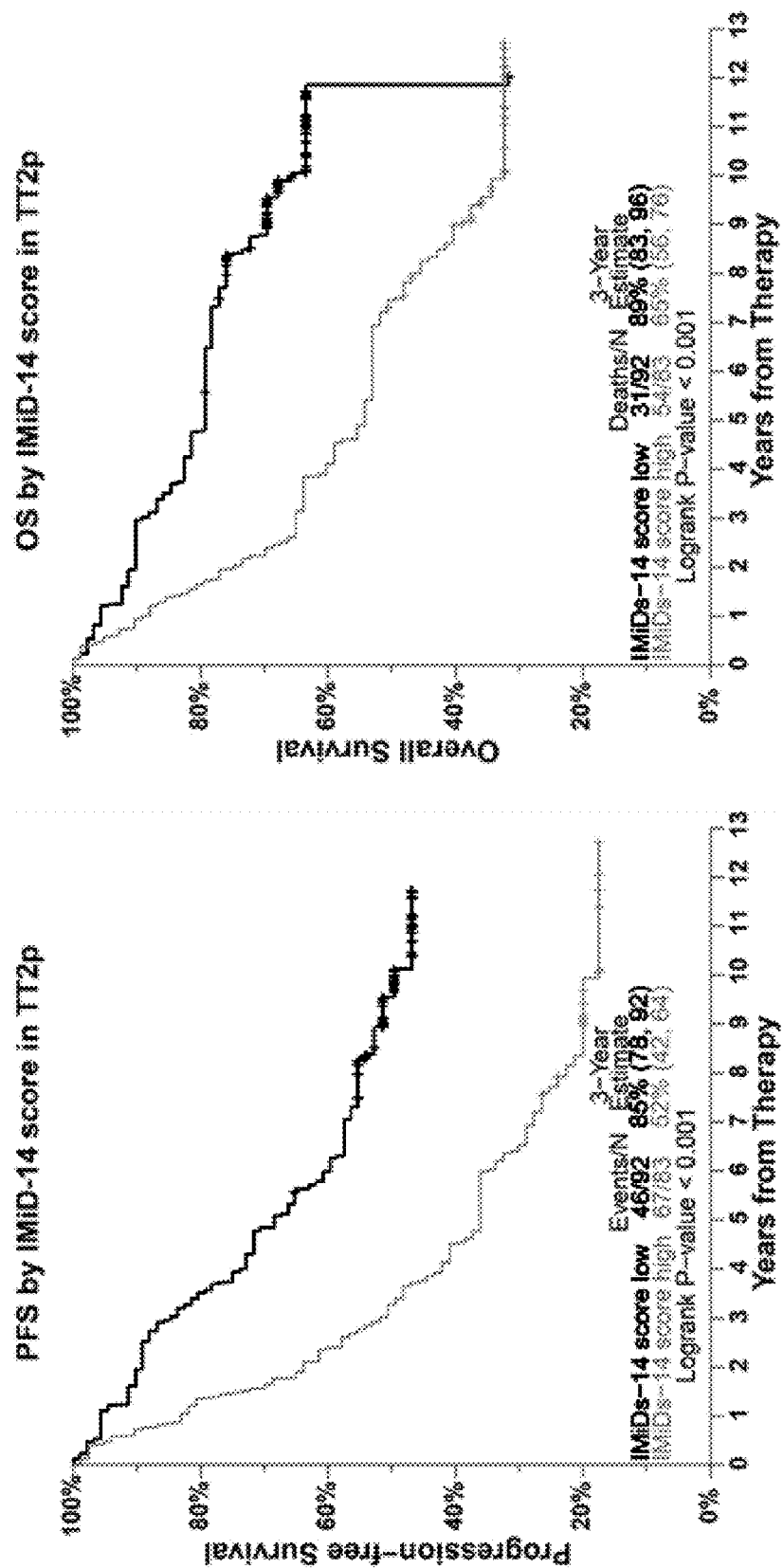
FIGS. 1A and 1B: Training set TT2p Thal arm (induction and consolidation with TD-PACE, maintenance with interferon and T). Kaplan-Meier (K-M) estimates in IMiD-14 high score (gray) showed inferior 3-year PFS (A) (52% vs. 85%, P<0.001) and OS (B) (65% vs. 89%, P<0.001) compared with IMiD-14 low score (black).

The present invention will now be described more fully hereinafter with reference to the accompanying drawings and specification, in which preferred embodiments of the invention are shown. This invention may, however, be embodied in different forms and should not be construed as limited to the embodiments set forth herein.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a non-viral vector) and the like, is meant to encompass variations of ±20%, ±10%, ±5%, ±1%, ±0.5%, or even ±0.1% of the specified amount.

As used herein, the transitional phrase "consisting essentially of" (and grammatical variants) means that the scope of a claim is to be interpreted to encompass the specified materials or steps recited in the claim, "and those that do not materially affect the basic and novel characteristic(s)" of the claimed invention. Thus, the term "consisting essentially of" when used in a claim of this invention is not intended to be interpreted to be equivalent to "comprising."

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

Immunomodulatory derivative (IMiD) as used herein refers to, as nonlimiting examples, thalidomide, lenalidomide and pomalidomide, derivatives thereof and analogs thereof, as well as any other agent identified as an IMiD, as is known in the art.

"Plasma cell disorder" refers to diseases and disorders resulting from abnormal proliferation of a monoclonal population of plasma cells. Plasma cell disorders include, but are not limited to, monoclonal gammopathy of undetermined significance (MGUS), multiple myeloma, solitary plasmacytoma of bone, extramedullary plasmacytoma, Waldenström's macroglobulinemia (WM), amyloidosis, light chain deposition disease, paraproteinemia, and heavy-chain disease. In particular embodiments of the present invention, the plasma cell disorder is multiple myeloma.

"Multiple myeloma" or "MM" refers to a cancer of plasma cells in the bone marrow. Uncontrolled growth of these plasma cells can lead to bone pain and fractures, anemia, infections, kidney failure and other complications. Risk factors for MM include drinking alcohol and obesity. Although treatable, remission may occur with treatment with steroids, chemotherapy and/or stem cell transplant.

According to the International Myeloma Working Group criteria, progressive disease (PD) is defined by at least a 25% increase from nadir in the serum paraprotein (absolute increase must be ≥0.5 g/dL) or urine paraprotein (absolute increase must be ≥200 mg/24 hours), or in the difference between involved and uninvolved serum-free light-chain (FLC) levels (with an abnormal FLC ratio and FLC difference >100 mg/L). In patients who lack measurable paraprotein levels (oligo- or nonsecretory myeloma), an increase in bone marrow plasma cells (≥10% increase) or new bone/soft tissue lesions increasing the size of existing lesions or unexplained serum calcium >11.5 mg/dL is used to define disease progression. Durie et al. *Leukemia* 2006; 20(9): 1467-1473. "Relapsed and refractory" myeloma is defined as progression of therapy in patients who achieve minor response (MR) or better, or who progress within 60 days of their last therapy. Patients who never achieve at least a MR to initial induction therapy and progress while on therapy are defined as "primary refractory." Relapsed myeloma is defined as disease in a myeloma patient who has previously been treated and has evidence of PD as defined here before, and who at the time of relapse does not meet the criteria for relapsed and refractory or primary refractory myeloma. Rajkumar et al. *Blood* 2011; 117(18):4691-4695.

The term "signature" may refer to a set of biological analytes, and the measurable quantities of said analytes, whose particular combination signifies the presence or absence of the specified biological state. These signatures are discovered in a plurality of subjects with known status (e.g., newly diagnosed MM patients or relapsed MM patients), and are discriminative (individually or jointly) of one or more categories or outcomes of interest. These measurable analytes, also known as biological markers, can be (but are not limited to) gene expression levels.

In some embodiments as set forth herein, the "signature" is a particular combination of genes whose expression levels, when incorporated into a classifier, discriminate a condition such as resistance to IMiDs treatment of MM from sensitivity to IMiDs treatment of MM.

The terms "classifier" and "predictor" may be used interchangeably and refer to a mathematical function that uses the values of the signature (e.g., gene expression levels for a defined set of genes) to generate scores for a given observation or individual patient for the purpose of assignment to a category.

A classifier as set forth herein may be obtained by a procedure known as "training," which makes use of a set of data containing observations with known category membership (e.g., prognosis-unfavorable or prognosis-favorable with respect to IMiDs resistance). More specifically, training seeks to find the optimal coefficient (i.e., weight) for each component of a given signature (e.g., gene expression level components), as well as an optimal signature, where the optimal result is determined by the highest achievable classification accuracy.

"Classification" refers to a method of assigning a subject, e.g., an MM patient, to one or more categories or outcomes (e.g., the IMiDs resistance or IMiDs sensitivity of an MM patient). The outcome, or category, is determined by the value of the scores provided by the classifier, which may be compared to a cut-off or threshold value, confidence level, or limit. In other scenarios, the probability of belonging to a particular category may be given (e.g., if the classifier reports probabilities).

The term "indicative" when used with gene expression levels, means that the gene expression levels are up-regulated or down-regulated, altered, or changed compared to the expression levels in alternative biological states (e.g., IMiDs resistance or IMiDs sensitivity). "Indicative" also signifies the ability to identify or distinguish the state of being of interest, for example, whether an MM patient has IMiDs resistance, or is at risk for having IMiDs resistance; determine whether an MM patient is developing, or is at risk for developing IMiDs resistance;

determine whether an MM patient has a poor prognosis for IMiDs treatment; or monitoring response to IMiDs treatment of an MM patient for IMiDs resistance.

The term "monitor," as used herein, generally refers to the overseeing, supervision, regulation, watching, tracking, or surveillance of an activity.

"Platform" or "technology" refers to an apparatus (e.g., instrument and associated parts, computer, computer-readable media comprising one or more databases as taught herein, reagents, etc.) that may be used to measure a signature, e.g., gene expression levels, in accordance with the present disclosure. An example of a platform includes, but is not limited to, an array platform.

The terms "array," "microarray" and "micro array" are interchangeable and refer to an arrangement of a collection of nucleotide sequences presented on a substrate. Any type of array can be utilized in the methods provided herein. For example, arrays can be on a solid substrate (a solid phase array), such as a glass slide, or on a semi-solid substrate, such as nitrocellulose membrane. Arrays can also be presented on beads, i.e., a bead array. These beads are typically microscopic and may be made of, e.g., polystyrene. The array can also be presented on nanoparticles, which may be made of, e.g., particularly gold, but also silver, palladium, or platinum. See, e.g., Nanosphere Verigene® System, which uses gold nanoparticle probe technology. Magnetic nanoparticles may also be used. Other examples include nuclear magnetic resonance microcoils. The nucleotide sequences can be DNA, RNA, or any permutations thereof (e.g., nucleotide analogues, such as locked nucleic acids (LNAs), and the like). In some embodiments, the nucleotide sequences span exon/intron boundaries to detect gene expression of spliced or mature RNA species rather than genomic DNA. The nucleotide sequences can also be partial sequences from a gene, primers, whole gene sequences, non-coding sequences, coding sequences, published sequences, known sequences, or novel sequences. The arrays may additionally include other compounds, such as antibodies, peptides, proteins, tissues, cells, chemicals, carbohydrates, and the like that specifically bind proteins or metabolites.

An array platform includes, but is not limited to, for example, an Affymetrix® microarray platform.

The term "sample" as used herein relates to a material or mixture of materials, typically, although not necessarily, in fluid form, containing one or more components of interest.

The term "biological sample" includes any sample, or portion thereof, that may be taken from a subject that contains genetic material that can be used in the methods provided herein. For example, a biological sample may include a sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, fractions and cells isolated from a mammal. Exemplary biological samples include but are not limited to cell lysate, a cell culture, a cell line, a tissue, oral tissue, gastrointestinal tissue, an organ, an organelle, a biological fluid, a blood sample, a urine sample, a skin sample, and the like. Particular biological samples include, but are not limited to, whole blood, partially purified blood, PBMCs, tissue biopsies, and the like. In some embodiments, the biological sample is a bone marrow, urine and/or blood sample. In some embodiments, the sample may comprise plasma cells obtained from bone marrow, urine and/or blood.

The term "genetic material" refers to a material used to store genetic information in the nuclei or mitochondria in cells from an organism. Examples of genetic material include, but are not limited to, double-stranded and single-stranded DNA, cDNA, RNA, and mRNA.

"Patient" or "subject" is used interchangeably. A patient or subject of this invention is any patient or subject with a cancer such as MM. In some embodiments, the subject is a human; however, a subject of this invention can include an animal subject, particularly mammalian subjects such as canines, felines, bovines, caprines, equines, ovines, porcines, rodents (e.g. rats and mice), lagomorphs, primates (including non-human primates), etc., including domesticated animals, companion animals and wild animals for veterinary medicine or treatment or pharmaceutical drug development purposes. The subjects relevant to this invention may be male or female and may be any species and of any race or ethnicity, including, but not limited to, Caucasian, African-American, African, Asian, Hispanic, Indian, etc., and combined backgrounds. The subjects may be of any age, including newborn, neonate, infant, child, adolescent, adult, and geriatric and male or female. In some embodiments of the invention, the subject has relapsed/refractory MM. In some embodiments, the subject does not have relapsed/refractory MM. In still other embodiments, the subject has undergone a hematopoietic stem cell transplant. In other embodiments, the subject has not undergone a hematopoietic stem cell transplant.

Unless otherwise defined, all technical terms used herein have the same meaning as commonly understood by one of ordinary skill in the art to which this disclosure belongs.

The present disclosure provides that variations in gene expression can be used to determine IMiDs resistance in a subject with a plasma cell disorder, such as multiple myeloma, with a high degree of accuracy.

The methods and assays of the present disclosure may be based upon gene expression, for example, through direct measurement of RNA, measurement of derived materials (e.g., cDNA), and measurement of RNA products (e.g., encoded proteins or peptides). Any method of extracting and screening gene expression may be used and is within the scope of the present disclosure.

In some embodiments, measuring includes the detection and quantification (e.g., semi-quantification) of mRNA in the sample. In some embodiments, the gene expression levels are adjusted relative to one or more standard gene level(s) ("normalized"). As known in the art, normalizing is done to remove technical variability inherent to a platform to give a quantity or relative quantity (e.g., of expressed genes).

It should be understood that there are many methods of mRNA quantification and detection that may be used by a platform in accordance with the methods disclosed herein.

The expression levels are typically normalized following detection and quantification as appropriate for the particular platform using methods routinely practiced by those of ordinary skill in the art. Examples of normalization methods include, but are not limited to, the Affymetrix Microarray Suite 5.0 (mas5.0), the perfect match only model of Li and Wong (Li and Wong (2001) *Proc. Natl. Acad. Sci. U.S.A.* 98, 31-36; Li and Wong (2001) *Genome Biol.* 2(8), research/0032.1) and the Robust Multi-array Analysis with [gcrma, (Wu et al. (2004) Working Papers, Department of Biostatistics, Johns Hopkins University)] and without [rma, (Irizarry et al. (2003) *Biostatistics* 4, 249-264.)] correction for GC content of the oligo. In some embodiments, the method used to normalize gene expression levels is the MAS 5.0 or Mas5 method. See Hubbell E, et al. Robust estimators for expression analysis, Bioinformatics, 2002, vol. 18 (pg. 1585-1592).

The MAS 5.0 signal is defined as the anti-log of a robust average (Tukey biweight) of the values $\log(PM_{ij}-CT_{ij})$, $j=1, \ldots, J$. To avoid taking the log of negative numbers, CT is defined as a quantity equal to MM when MM<PM, but adjusted to be less than PM when MM≥PM, which in general occurs for about one-third of all probes. A model for MAS 5.0 is $\log(PM_{ij}-CT_{ij})=\log(\theta_i)+\epsilon_{ij}$, $j=1, \ldots, J$. In addition to MAS 5.0, there are other microarray normalization methods such as RMA, GCRMA, and Li-Wong method that can be employed and used without undue experimentation.

With mRNA detection and quantification and a matched normalization methodology in place for a platform, it is a matter of using carefully selected and adjudicated patient samples for the training methods. These subject-samples may be used to generate coefficients, thresholds and cut-offs for a test implemented using a different mRNA detection and quantification platform. For example, an optimal cut-off determined for an IMiDs-based risk score (IMiD-14) using the average log-scale difference in gene expression of 4 prognosis-unfavorable genes (hazard ratio [HR]>1, XPO1, DDR2, TRAF3IP3, FAIM3) for IMiDs resistance and 10 prognosis-favorable genes (HR<1, KIAA0247, SLC39A14, PGRMC2, LAMA5, FLJ22531, ITGA6, ENO2, AMPD1, TNFRSF7, IL5RA), normalized with the mas5.0 method, has been established as −1.075. Thus, an IMiD-14 score determined for a sample from a MM patient that is higher than this number is an indication that the patient is at risk for IMiDs resistance.

The present disclosure further provides methods for: determining whether a patient having a plasma cell disorder, such as an MM patient, has IMiDs resistance, or is at risk for having IMiDs resistance; determining whether the patient is developing, or is at risk for developing IMiDs resistance; determining whether a patient having a plasma cell disorder, such as an MM patient, has a poor prognosis for IMiDs treatment; or monitoring response to IMiDs treatment of a patient having a plasma cell disorder, such as an MM patient, for IMiDs resistance. The method for making this determination relies upon the use of a classifier. The methods may include: a) measuring the expression levels of pre-defined sets of genes, for example, prognosis-favorable genes for IMiDs resistance and prognosis-unfavorable genes for IMiDs resistance; b) normalizing gene expression levels for the technology used to make said measurement; c) taking those values and obtaining a IMiDs resistance classifier; d) comparing the classifier to a pre-defined threshold or cut-off value that indicates likelihood of IMiDs resistance to: determine whether a patient having a plasma cell disorder, such as an MM patient, has IMiDs resistance, or is at risk for having IMiDs resistance; determine whether a patient having a plasma cell disorder, such as an MM patient, is developing, or is at risk for developing IMiDs resistance; determine whether a patient having a plasma cell disorder, such as an MM patient, has a poor prognosis for IMiDs treatment; or monitoring response to IMiDs treatment of a patient having a plasma cell disorder, such as an MM patient, for IMiDs resistance.

The classifiers that are developed during training and using a training set of samples are applied for prediction purposes to diagnose new individuals ("classification"). For each subject or patient, a biological sample is taken and the normalized levels of expression (i.e., the relative amount of mRNA expression) in the sample of each of the genes specified by the signatures found during training are the input for the classifiers. As outputs, the classifiers can be used to determine the likelihood of IMiDs resistance to: determine whether a patient having a plasma cell disorder, such as an MM patient, has IMiDs resistance, or is at risk for having IMiDs resistance; determine whether a patient having a plasma cell disorder, such as an MM patient, is developing, or is at risk for developing IMiDs resistance; determine whether a patient having a plasma cell disorder, such as an MM patient, has a poor prognosis for IMiDs treatment; or monitoring response to IMiDs treatment of a patient having a plasma cell disorder, such as an MM patient, for IMiDs resistance.

In one embodiment, the present invention provides a method for identifying whether a subject having or suspected of having a plasma cell disorder has, or is at risk of developing immunomodulatory derivatives (IMiDs) resistance, comprising: measuring gene expression levels of prognosis-favorable genes for IMiDs response and gene expression levels for prognosis-unfavorable genes for IMiDs response in a sample obtained from the subject; normalizing the gene expression level of prognosis-favorable genes for IMiDs response to obtain a normalized gene expression level for prognosis-favorable genes for IMiDs response and normalizing the gene expression level of prognosis-unfavorable genes IMiDs response to obtain a normalized gene expression level for prognosis-unfavorable genes IMiDs response; obtaining a difference between the normalized gene expression level for prognosis-favorable genes for IMiDs response and the normalized gene expression level for prognosis-unfavorable genes IMiDs response to provide a gene expression profile (GEP) or signature; and comparing the gene expression profile or signature to a pre-defined threshold or cut-off value, wherein if the gene expression profile or signature exceeds the threshold or cut-off value, the gene expression profile is indicative that the subject has, or is at risk of developing IMiDs resistance.

In a further embodiment, the present invention provides a method of identifying a subject having or suspected of having a plasma cell disorder as having a poor prognosis for IMiDs treatment, comprising: measuring gene expression levels of prognosis-favorable genes for IMiDs response and gene expression levels for prognosis-unfavorable genes for IMiDs response in a sample obtained from the subject; normalizing the gene expression level of prognosis-favorable genes for IMiDs response to obtain a normalized gene expression level for prognosis-favorable genes for IMiDs response and normalizing the gene expression level of prognosis-unfavorable genes IMiDs response to obtain a normalized gene expression level for prognosis-unfavorable genes IMiDs response; obtaining a difference between the normalized gene expression level for prognosis-favorable genes for IMiDs response and the normalized gene expression level for prognosis-unfavorable genes IMiDs response to provide a gene expression profile or signature; and comparing the gene expression profile to a pre-defined threshold or cut-off value, wherein if the gene expression profile exceeds the threshold or cut-off value, the gene expression profile identifies that the subject has a poor prognosis for IMiDs treatment.

In an additional embodiment, the present invention provides a method of identifying a subject with a plasma cell disorder that will not respond to treatment with IMiDs, comprising: measuring gene expression levels of prognosis-favorable genes for IMiDs response and gene expression levels for prognosis-unfavorable genes for IMiDs response in a sample obtained from the subject; normalizing the gene expression level of prognosis-favorable genes for IMiDs response to obtain a normalized gene expression level for prognosis-favorable genes for IMiDs response and normalizing the gene expression level of prognosis-unfavorable genes IMiDs response to obtain a normalized gene expression level for prognosis-unfavorable genes IMiDs response; obtaining a difference between the normalized gene expression level for prognosis-favorable genes for IMiDs response and the normalized gene expression level for prognosis-unfavorable genes IMiDs response to provide a gene expression profile or signature; and comparing the gene expression profile to a pre-defined threshold or cut-off value, wherein if the gene expression profile exceeds the threshold or cut-off value, the gene expression profile identifies the subject as a subject who will not respond to treatment with IMiDs.

In the methods described herein, prognosis-unfavorable genes for IMiDs response comprise, consist essentially of and/or consist of one or more (e.g., at least one, at least two, at least three, at least four) of the following genes: XPO1, DDR1, TRAFIP3 and FAIM3, in any combination.

In the methods described herein, the prognosis-favorable genes for IMiDs response comprise, consist essentially of and/or consist of one or more (e.g., at least one, at least two, at least three, at least four, at least five, at least six, at least seven, at least eight, at least nine, at least ten) of the following genes: KIAA0247, SLC39A14, PGRMC2, LAMA5, FLJ22531, ITGA6, ENO2, AMPD1, TNFRSF7 and IL5RA, in any combination.

In the methods described herein, the gene expression level of prognosis-favorable genes for IMiDs response and the gene expression level of prognosis-unfavorable genes for IMiDs response is normalized by the MAS5 method.

In the methods described herein, the pre-defined cut-off value can be −1.075 and/or the pre-defined threshold value can be −1.075.

In the methods described herein, the gene expression profile or signature can be calculated using the following equation:

$$GEP = [(\log_2(205168\_at) + \log_2(208775\_at) + \\ \log_2(213888\_s\_at) + \log_2(221601\_s\_at))/4] - \\ [(\log_2(201313\_at) + \log_2(201656\_at) + \log_2(201701\_s\_at) + \\ \log_2(202181\_at) + \log_2(204922\_at) + \log_2(206121\_at) + \\ \log_2(206150\_at) + \log_2(210150\_s\_at) + \\ \log_2(210744\_s\_at) + \log_8(212110\_at))/10].$$

In the methods described herein the plasma cell disorder can be multiple myeloma (MM). In some embodiments, the subject can have relapsed/refractory MM and in some embodiments, the subject does not have relapsed/refractory MM.

In some embodiments of the methods of this invention, the subject can be undergoing and/or has undergone a hematopoietic stem cell transplant.

In some embodiments, the subject is not undergoing and/or has not undergone a hematopoietic stem cell transplant.

The methods of this invention can further comprise, consist essentially of and/or consist of the step of treating the subject with a non-IMiD therapy, selected from the group consisting of: a) bortezomib-dexamethasone (VD); b) bortezomib-cyclophosphamide-dexamethasone with daratumumab (CyBorD-Dara); c) bortezomib-cyclophosphamide-dexamethasone without daratumumab (CyBorD); d) carfilzomib-cytoxan-dexamethasone (Car-Cy-Dex); e) bortezomib-melphalan-prednisone with daratumumab (VMP-Dara); f) bortezomib-melphalan-prednisone without daratumumab (VMP); g) bortezomib-dexamethasone-cisplatin-Adriamycin-cyclophosphamide-etoposide (VD-PACE); and h) any combination of (a)-(g). The methods of this invention can further comprise the step of treating the subject with any other non-IMiD therapy, as would be known in the art.

The present invention additionally provides a method of treating a plasma cell disorder in a subject (e.g., a subject in need thereof), comprising administering to the subject having resistance to IMiD therapy an effective amount of a non-IMiD therapy. A subject can be determined to have resistance to IMiD therapy according to the methods described herein. Thus, in some embodiments, the present invention provides a method of treating a plasma cell disorder in a subject identified as having resistance to IMiD therapy according to the methods of this invention, comprising administering to the subject an effective amount of a non-IMiD therapy.

As used herein, a "non-IMiD therapy" is a therapy that does not include an IMiD. For example, the therapy can exclude any of thalidomide, lenalidomide and pomalidomide, derivatives thereof and analogs thereof, as well as any other agent identified as an IMiD, in any combination, or all together. Thus, in some embodiments, the therapy can include one or more of thalidomide, lenalidomide and pomalidomide, derivatives thereof and analogs thereof, as well as any other agent identified as an IMiD, in any combination and exclude thalidomide, lenalidomide and pomalidomide, derivatives thereof and analogs thereof, as well as any other agent identified as an IMiD, in any combination.

In some embodiments, the non-IMiD therapy can be a) bortezomib-dexamethasone (VD), b) bortezomib-cyclophosphamide-dexamethasone with daratumumab (CyBorD-Dara), c) bortezomib-cyclophosphamide-dexamethasone without daratumumab (CyBorD), d) carfilzomib-cytoxan-dexamethasone (Car-Cy-Dex), e) bortezomib-melphalan-prednisone with daratumumab (VMP-Dara), bortezomib-melphalan-prednisone without daratumumab (VMP), g) bortezomib-dexamethasone-cisplatin-Adriamycin-cyclophosphamide-etoposide (VD-PACE); and h) any combination of (a)-(g).

It is to be understood that the invention is not limited in its application to the details of construction and the arrangement of components set forth in the following description or illustrated in the following drawings. The invention is capable of other embodiments and of being practiced or of being carried out in various ways.

The following examples are illustrative only and are not intended to be limiting in scope.

EXAMPLES

The following EXAMPLES provide illustrative embodiments. Certain aspects of the following examples are disclosed in terms of techniques and procedures found or contemplated by the present inventors to work well in the practice of the embodiments. In light of the present disclosure and the general level of skill in the art, those of skill will appreciate that the following examples are intended to be exemplary only and that numerous changes, modifications, and alterations can be employed without departing from the scope of the presently claimed subject matter.

Example 1

Clinical and pharmacogenomic data from MM patients who received test doses of thalidomide (Thal), lenalidomide (Len) or pomalidomide (Pom) to identify genes that were related to IMiD response were used to build an IMiD-resistance gene profile/signature. IMiDs and proteasome inhibitors are two types of agents used in current MM chemotherapy. By combining the IMiD-resistance signature with the proteasome inhibitor-resistance signature (GEP80), it was shown that patients resistant to both drugs had the worst outcome.

GEP-based pharmacogenomics of paired CD138-purified plasma cells, obtained from patients prior to and 48 hours after administration of test doses of Thal (42 newly diagnosed MM), Len (18 relapsed/refractory MM), or Pom (18 relapsed/refractory MM) were compared using significance analysis of microarrays (SAM). Genes that had expression levels significantly changed after 48 hours in all three IMiDs (P<0.05 by SAM analysis and with change in same direction) were considered as IMiD response genes.

The total therapy (TT)2 trial Thal arm (newly diagnosed MM patients, induction and consolidation with T[Thal]D-PACE, maintenance with interferon and T until progression or intolerance) data were used as the training set. Baseline GEPs and progression-free survival (PFS) data were combined for building an IMiD-resistance gene signature. IMiD response genes that had P values less than 0.05 based on univariate Cox regression analysis for PFS in the training set were used to calculate the IMiDs resistance score, which was the difference between the average log 2-scale expression of prognosis-unfavorable (hazard ratio [HR]>1) and prognosis-favorable (HR<1) genes. An optimal cutoff for the IMiDs resistance score was then established with the running log-rank test, so that patients with scores higher than the cutoff were considered as IMiDs resistant patients.

Four independent MM data sets were used as validation, of which both baseline GEPs of purified plasma cells and survival data were available. All of them are from clinical trials in which patients received IMiDs containing regimens, including TT3a (newly diagnosed MM patients, induction with VTD-PACE, and maintenance with VTD in the 1 year followed by TD for 2 years), TT3b (newly diagnosed MM patients, induction with VTD-PACE, and maintenance with VR[Len]D for 3 years), TT6 (pretreated MM patients, induction with VTD-PACE, and maintenance with VRD or VMD for 3 years), and HOVON65/GMMG-HD4 trial VAD arm (newly diagnosed MM patients, induction with VAD, and maintenance with T for 2 years). The IMiDs resistant group in TT2 (Thal arm) training set exhibited significantly poorer PFS (P<0.001) and inferior OS (P<0.001) than the IMiDs sensitive group. Next, we examined whether this model had outcome discriminatory power in several independent test cohorts treated with IMiDs. In validation cohort TT3a (induction and consolidation with VT(thalidomide)D-PACE, maintenance with VTD in the 1st year followed by TD for 2 years), 3-year PFS and OS rates for the predicted IMiDs resistant patients were 63% and 71%, whereas the IMiDs sensitive patients were 87% and 90%, both PFS and OS were significantly different between the two groups (PFS P=0.01, OS P<0.001). In validation cohort TT3b (induction and consolidation with VT(thalidomide)D-PACE, maintenance with VR(lenalidomide)D for 3 years), 3-year PFS and OS rates for the predicted IMiDs resistant patients were 62% and 70%, whereas the IMiDs sensitive patients were 80% and 85%, both PFS and OS were significantly different between the two groups (PFS P=0.002, OS P=0.003). In validation cohort HOVON65/GMMG-HD4 VAD arm (induction with vincristine, doxorubicin, and dexamethasone, and maintenance with thalidomide for 2 years), 3-year PFS and OS rates for the predicted IMiDs resistant patients were 16% and 38%, whereas the IMiDs sensitive patients were 54% and 82%, both PFS and OS were significantly different between the two groups (PFS P<0.001, OS P<0.001). Also, the IMiDs resistance scores of TT2-Thal relapse samples were significantly higher than those of TT2-Thal baseline samples.

Plasma cell purifications and GEP, using the Affymetrix U133 Plus 2.0 microarray, were performed as previously described (Ref: Zhan F, Huang Y, Colla S, et al. The molecular classification of multiple myeloma. Blood. 2006; 108:2020-2028.). Samples were hybridized to Affymetrix expression arrays. Affymetrix U133Plus2.0 arrays were used in the pomalidomide study and Affymetrix U95Av2 arrays were used for thalidomide and lenalidomide pharmacogenomics studies. Bone marrow samples from MM patients enrolled in pharmacogenomics study were obtained prior to, and 48 hours after administration of a test dose of thalidomide (n=42 newly diagnosed), lenalidomide (n=18 relapsed/refractory) or pomalidomide (n=18 relapsed refractory). Plasma cell isolation from mononuclear cell fraction was performed by immunomagnetic bead selection with monoclonal anti-human CD138 antibody using the AutoMACS automated separation system (Miltenyi-Biotec) as previously described. Isolated bone marrow plasma cells were processed and analyzed for Gene-expression profiling (GEP) according to previously reported methods. Samples were hybridized to an Affymetrix U133Plus2.0 microarray for pomalidomide study and to an Affymetrix U95Av2 microarray for thalidomide and lenalidomide studies according to the manufacturer's recommendations and then read on GeneChip Scanner 3000 (Affymetrix). The data files were deposited in the ArrayExpress archive under the accession number E-TABM-1138.

|  | Thalidomide | Lenalidomide | Pomalidomide |
|---|---|---|---|
| Multiple myeloma | Newly diagnosed | Relapsed refractory | Relapsed refractory |
| Clinical trial | Thal arm of Total Therapy 2 | Salvage single agent | Response adaptive phase II |
| Number of patients | 42 | 18 | 18 |
| Dose, mg/d | 400 | 25 to 50 | 4 |
| Probe sets changed (p < 0.05) after 48 hr of IMiD treatment | 1398 | 1304 | 4944 |

SAM analysis identified 176 genes whose expression levels significantly changed in the same direction 48 hours after the IMiD test dose relative to baseline by applying significance analysis of microarrays [SAM] using a P-value 0.05. Each of these genes were correlated with PFS in thalidomide arm of TT2 trial (induction and consolidation with TD-PACE, maintenance with interferon and T) in a Cox regression model and ranked the genes by P values. From these identified genes, 14 genes were selected that had P values <0.05 based on univariate Cox regression analysis for PFS. These 14 genes were combined to create a continuous score for each patient, defined as the average log-scale differential expression of the 4 prognosis-unfavorable (hazard ratio [HR]>1) and the 10 prognosis-favorable (HR<1) genes. An optimal cutoff for this dichotomized IMiDs-based risk score (IMiD-14) was then established with the running log-rank test as −1.075, so that patients with scores higher than the cutoff were considered as IMiDs resistant patients. GEP data was normalized with the MAS5 method and the IMiD-14 score was calculated using the following equation to obtain a difference in normalized expression between prognosis-favorable gene expression and prognosis-unfavorable gene expression using base 2 logarithms of signal intensities observed for probes for the 4 prognosis-unfavorable genes and the 10 prognosis-favorable genes:

$$IMid\text{-}14 \text{ score} = [(\log_2(205168\_at) + \\ (\log_2(208775\_at) + \log_2(213888\_s\_at) + \log_2(221601\_s\_at))/4] - \\ [(\log_2(201313\_at) + \log_2(201656\_at) + \log_2(201701\_s\_at) + \\ \log_2(202181\_at) + \log_2(204922\_at) + \log_2(206121\_at) + \\ \log_2(206150\_at) + \log_2(210150\_s\_at) + \\ \log_2(210744\_s\_at) + \log_s(212110\_at))/10]$$

Figure 2B:
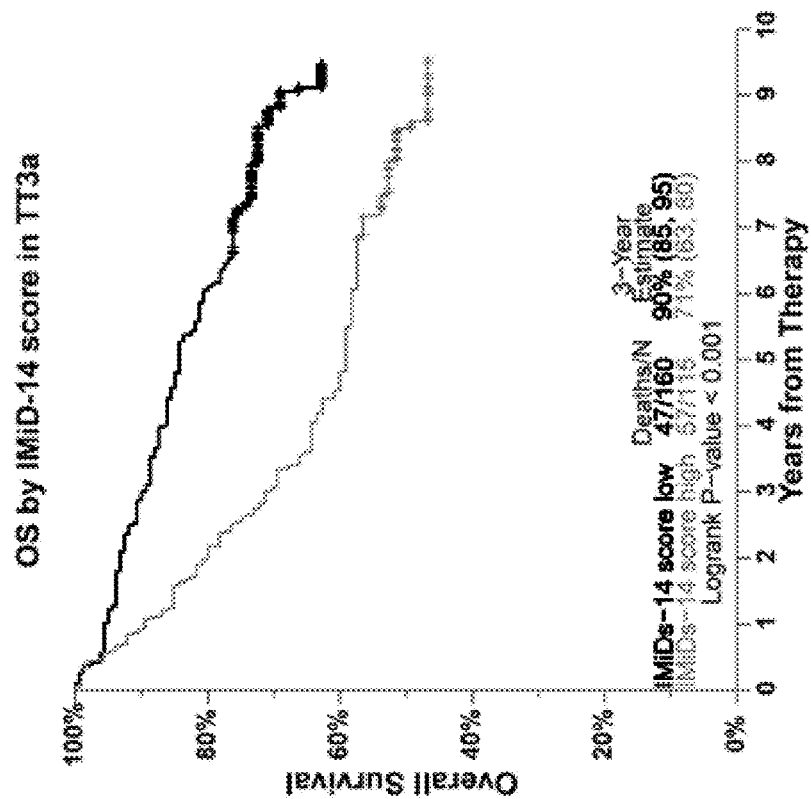
FIGS. 2A and 2B: Validation cohort TT3a (induction with VTD-PACE, and maintenance with VTD for 1 year followed by TD for 2 years). K-M estimates in IMiD-14 high score (gray) showed inferior 3-year PFS (A) (63% vs. 87%, P=0.01) and OS (B) (71% vs. 90%, P<0.001) compared with IMiD-14 low score (black).
Figure 2A:
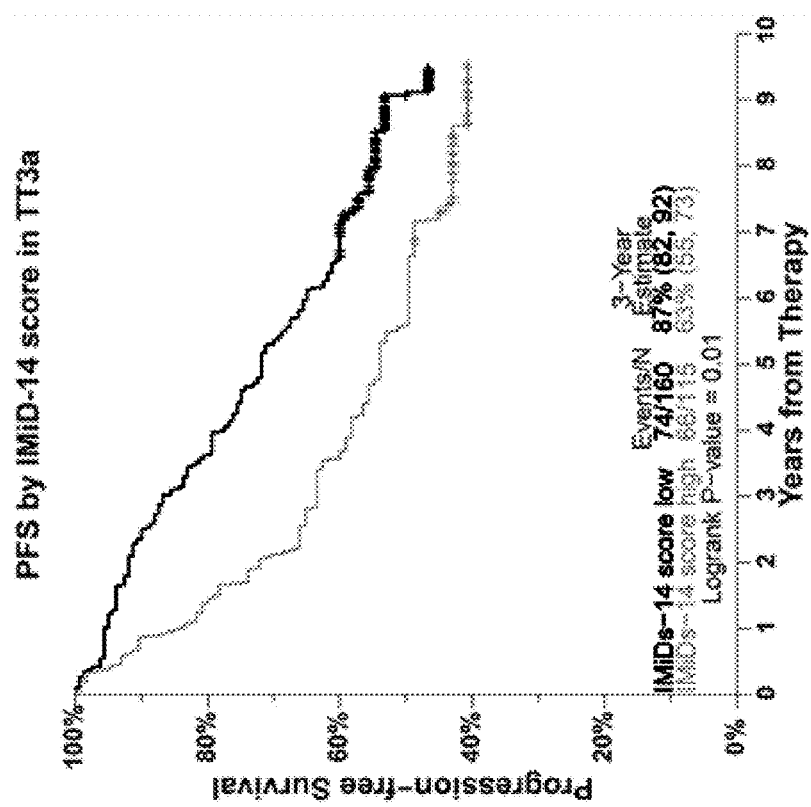
Figures 3A, 3B:
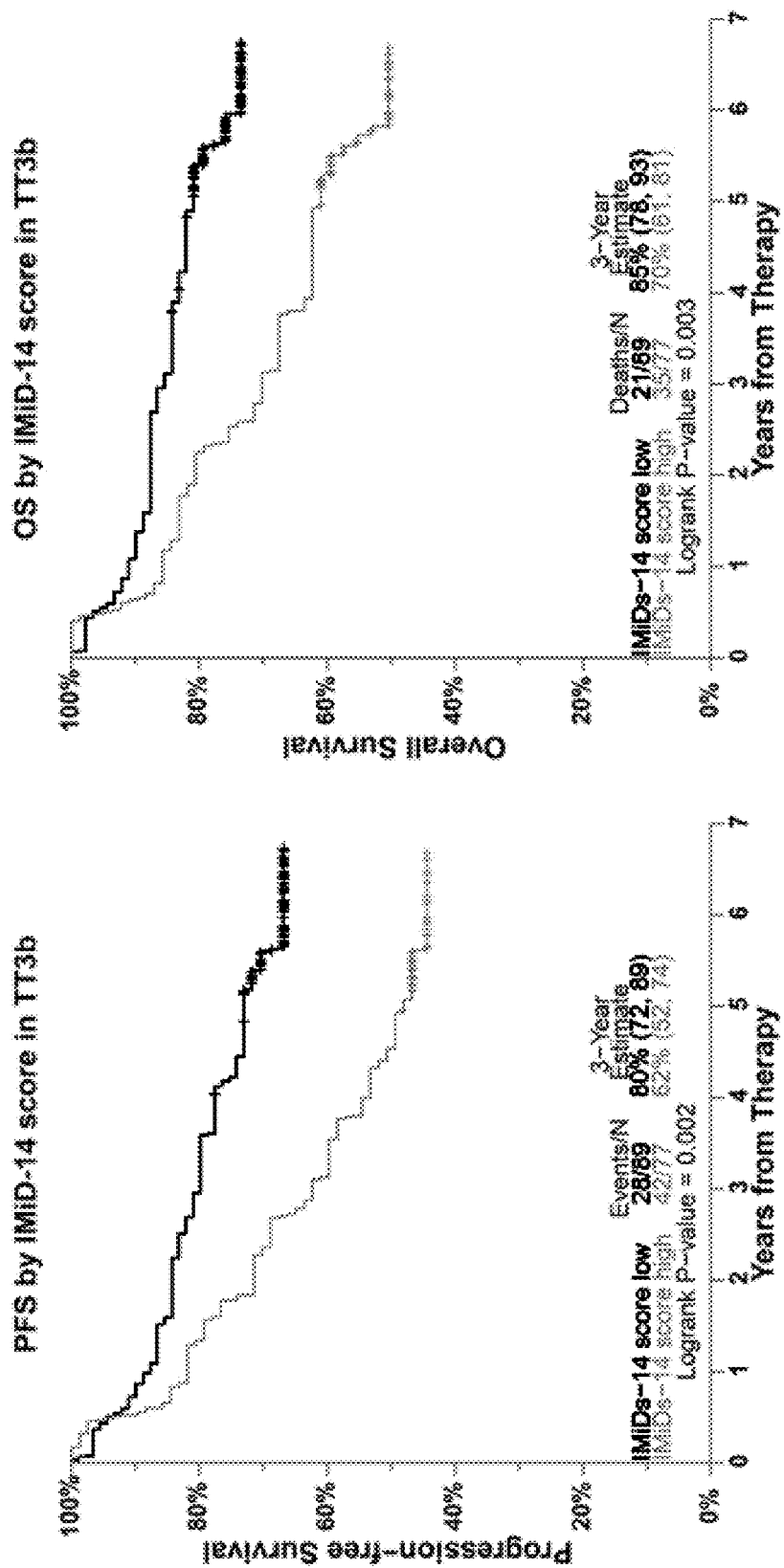
FIGS. 3A and 3B: Validation cohort TT3b (induction with VTD-PACE, and maintenance with VRD for 3 years). K-M estimates in IMiD-14 high score (gray) showed inferior 3-year PFS (A) (62% vs. 80%, P=0.002) and OS (B) (70% vs. 85%, P=0.003) compared with IMiD-14 low score (black).
Figures 4A, 4B:
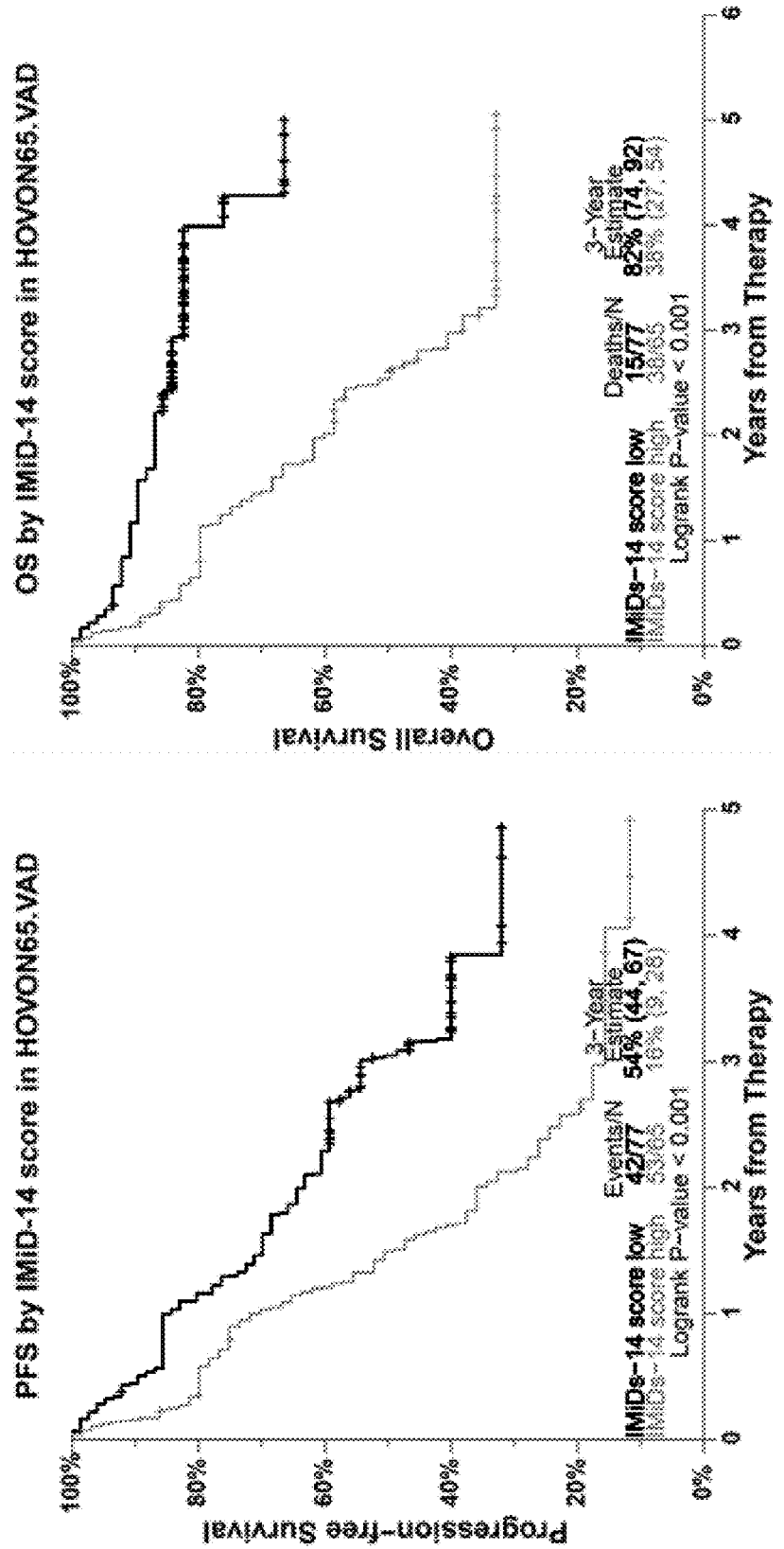
FIGS. 4A and 4B: Validation cohort HOVON65/GMMG-HD4 VAD arm (induction with VAD, and maintenance with thalidomide for 2 years). K-M estimates in IMiD-14 high score (gray) and IMiD-14 low score (black) showed inferior 3-year PFS (A) (16% vs. 54%, P<0.001) and OS (B) (38% vs. 82%, P<0.001)
Figure 6B:
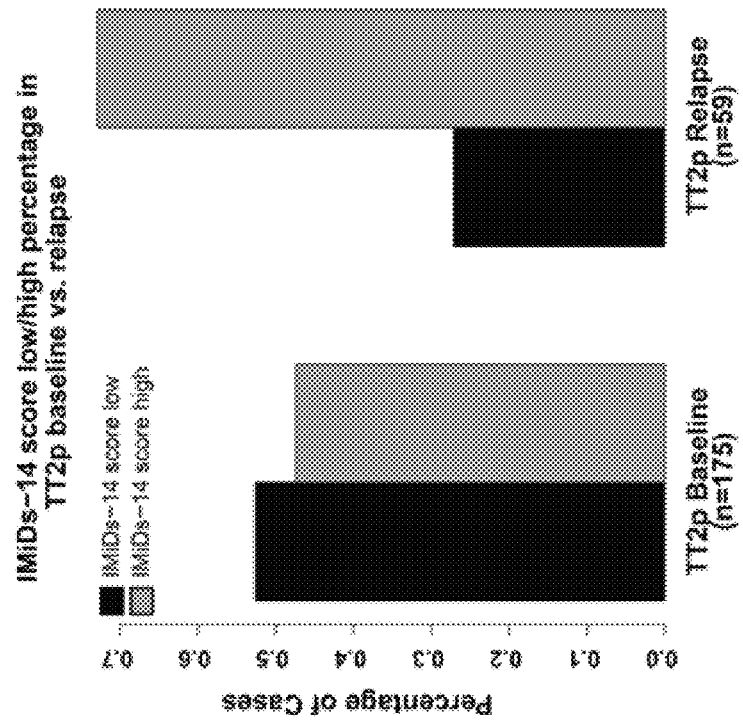
FIGS. 6A and 6B: IMiD-14 score for newly diagnosed and relapsed MM patients. Among relapsed patients in TT2p, the IMiD-14 score was significantly higher (A) compared with newly diagnosed patients, and was represented by high frequency of IMiD-14 high risk vs. IMiD-14 low risk (B).
Figure 6A:
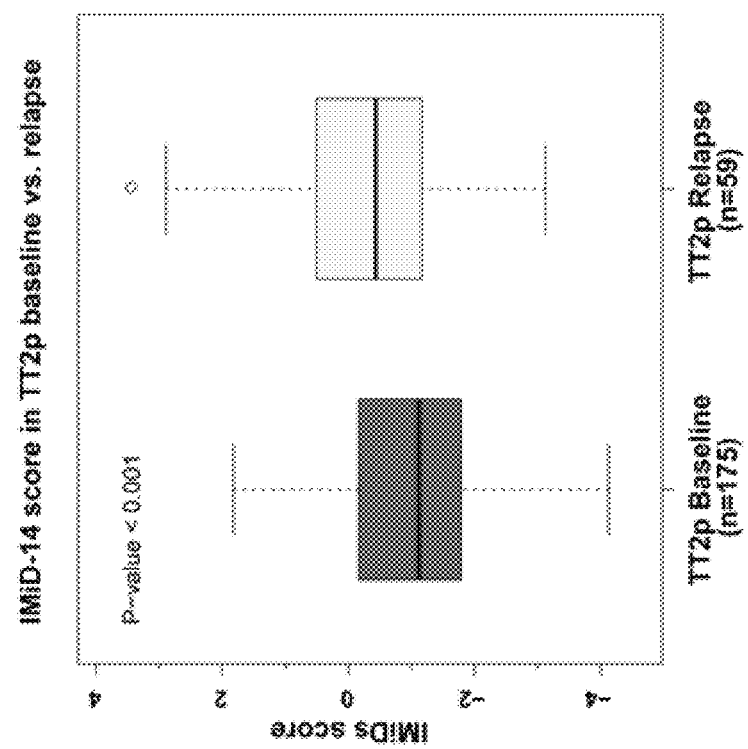

Patients having scores greater than the cutoff point (IMiD-14 high) were deemed to have IMiD-resistant disease and patients with scores below the cut point (IMiD-14 low) as IMiD-sensitive disease. After cross validation, the IMiD-14 genes were applied to the entire training set in TT2 (thalidomide arm). Results showed significant survival difference in the two groups. In the training set, patients with IMiD-14 high score had PFS and OS of 52% and 65%, respectively compared with corresponding rates of 85% and 89% (P<0.001) in IMiD-14 low score patients (FIGS. 1A and 1B). We then examined the independent prognostic/predictive value of IMiD-14 gene signature in other clinical trials in which patients were treated with IMiDs. In validation cohort TT3a (induction with VT(thalidomide)D-PACE, and maintenance with VTD in the 1 year followed by TD for 2 years), there were significant differences in outcome between patients whom IMiD-14 model predicted to have IMiDs resistance versus others, 3-year PFS and OS rates for the predicted IMiDs resistant patients were 63% and 71%, whereas for the rest of patients the corresponding rates were 87% and 90% (FIGS. 2A and 2B, PFS P=0.01, OS P<0.001). In validation cohort TT3b (induction with VT(thalidomide) D-PACE, and maintenance with VRD for 3 years), 3-year PFS and OS rates for the predicted IMiDs resistant patients were 62% and 70%, whereas for the rest of patients the corresponding rates were 80% and 85% (FIGS. 3A and 3B, PFS P=0.002, OS P=0.003). The discriminatory power of IMiD-14 was also independently confirmed in the validation cohort HOVON65/GMMG-HD4 VAD arm (induction with vincristine, doxorubicin, and dexamethasone, and maintenance with thalidomide for 2 years), 3-year PFS and OS rates for the predicted IMiDs resistant patients were 16% and 38%, versus 54% and 82%, respectively for the rest of the patients (FIGS. 4A and 4B, PFS P<0.001, OS P<0.001). Lastly, in the validation cohort TT6 (pretreated MM patients, induction with VTD-PACE and maintenance with VRD or VMD for 3 years), 3-year, 3-year PFS and OS rates for the predicted IMiDs resistant patients were 39% and 49%, versus 74% and 83%, respectively for the rest of the patients (FIGS. 5A and 5B, PFS P=0.026, OS P=0.001). IMiDs resistance scores were determined for TT2p relapse patients. The IMiDs resistance scores for samples from TT2p relapse patients was significantly higher than IMiDs resistance scores exhibited by samples from the TT2p baseline (newly diagnosed MM patients) group (FIGS. 6A and 6B).

Figure 7A:
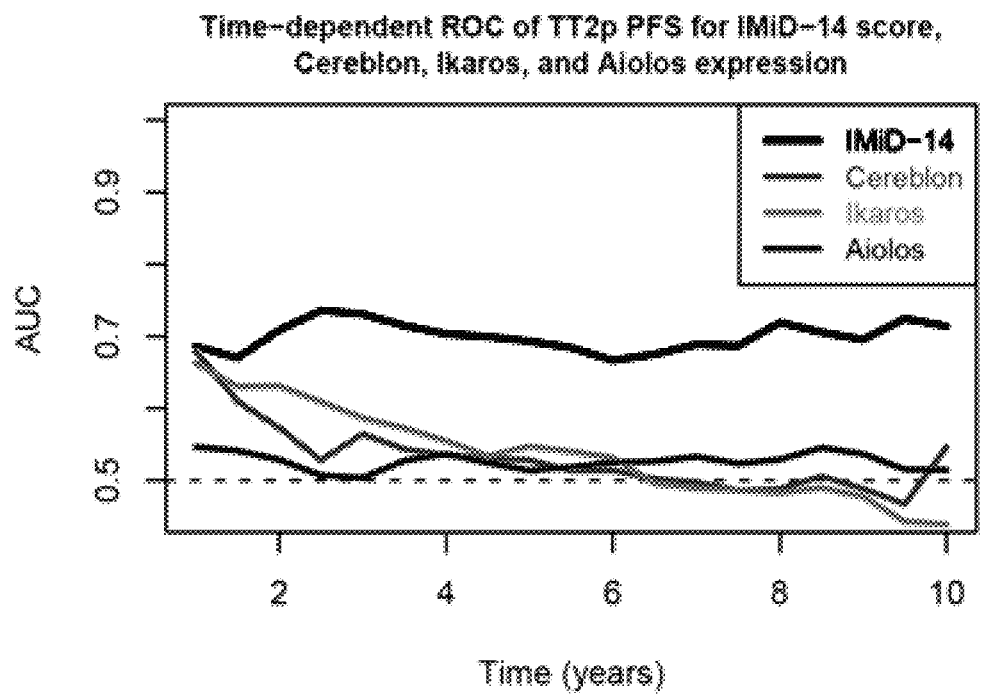
FIGS. 7A, 7B, 7C, 7D, 7E, 7F, 7G and 7H: Time-dependent ROC curves for IMiD-14 model, cereblon, Ikaros, and Aiolos. (A) TT2 thalidomide arm PFS data, (B) TT2 thalidomide arm OS data, (C) TT3a PFS data, (D) TT3a OS data, (E) TT3b PFS data, (F) TT3b OS data, (G) HOVON65/GMMG-HD4 VAD arm PFS data, (H) HOVON65/GMMG-HD4 VAD arm OS data.
Figure 7B:
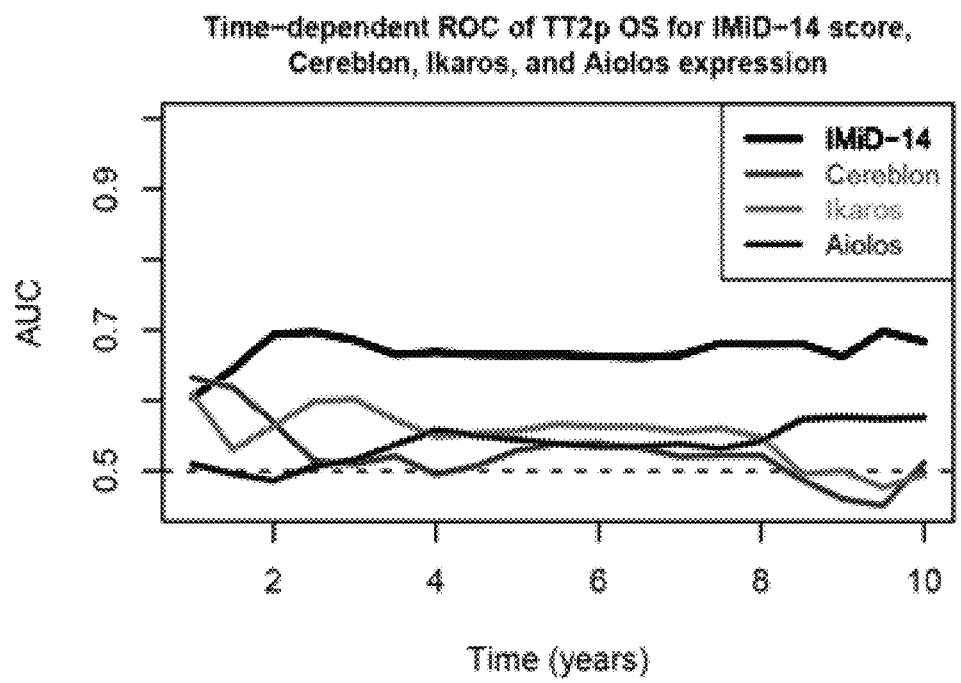
Figure 7C:
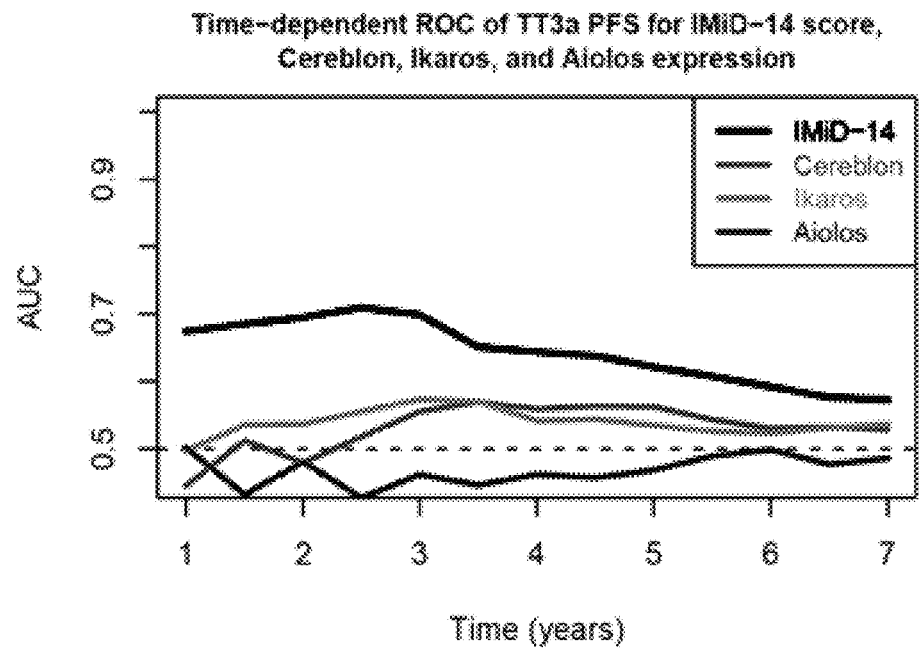
Figure 7D:
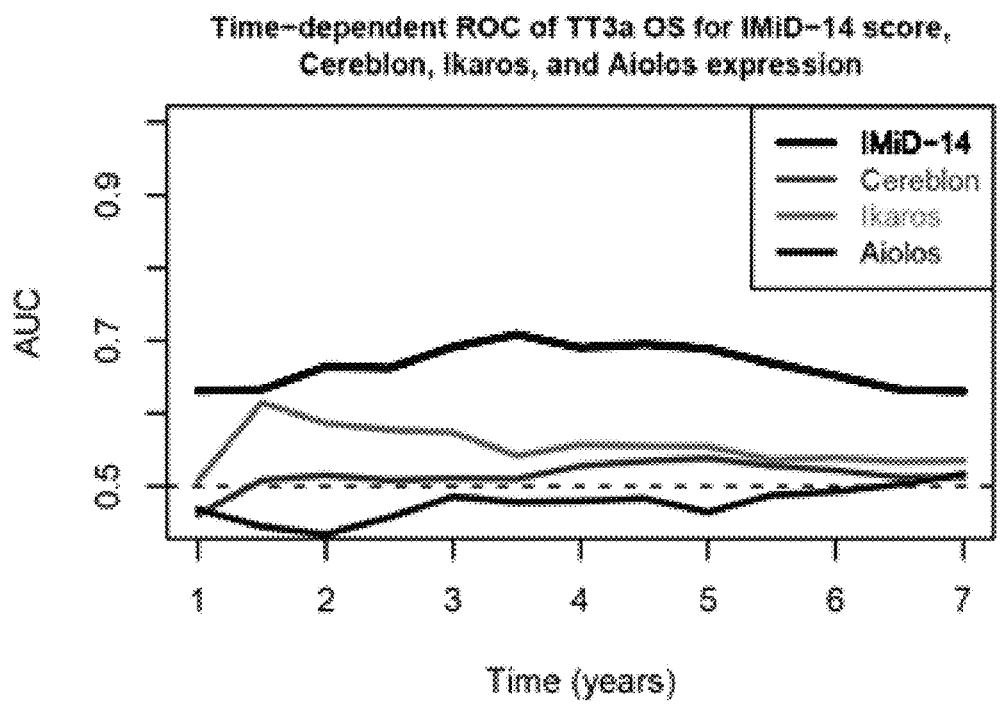
Figure 7E:
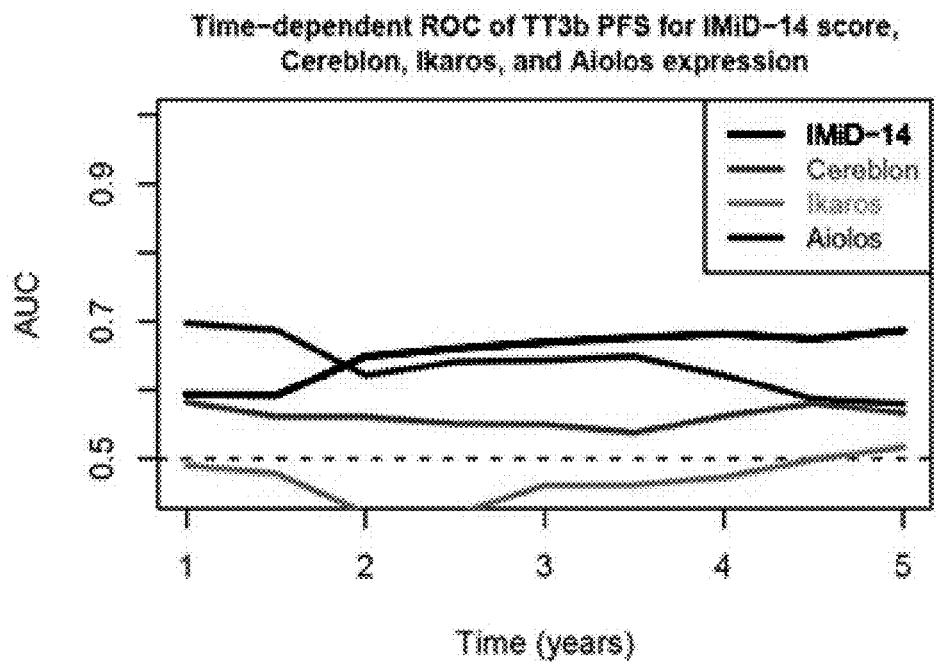
Figure 7F:
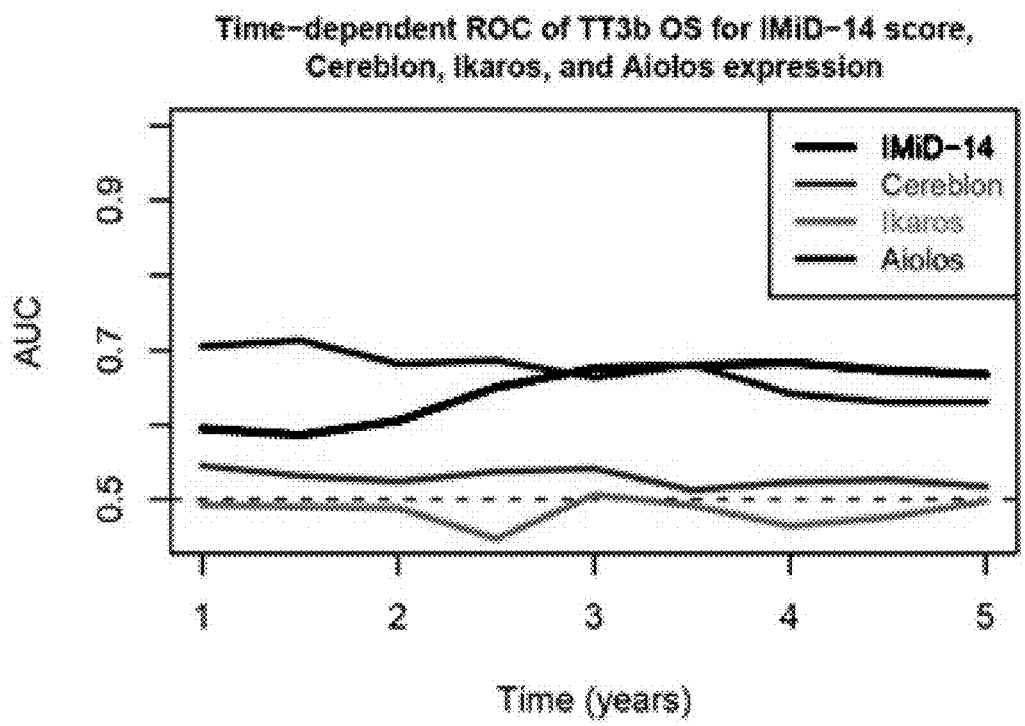
Figure 7G:
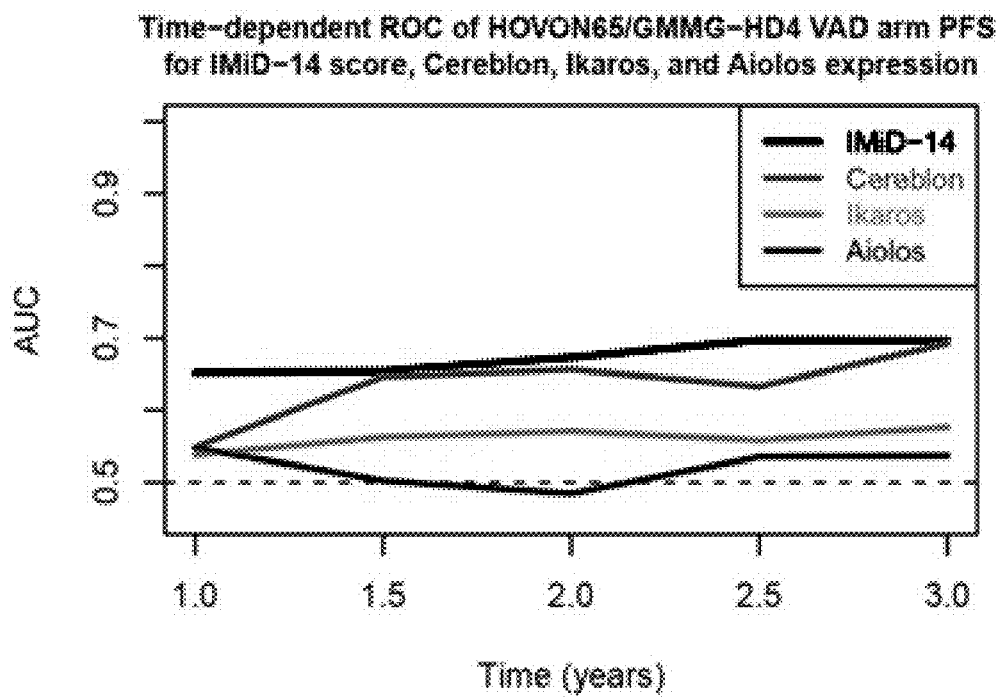
Figure 7H:
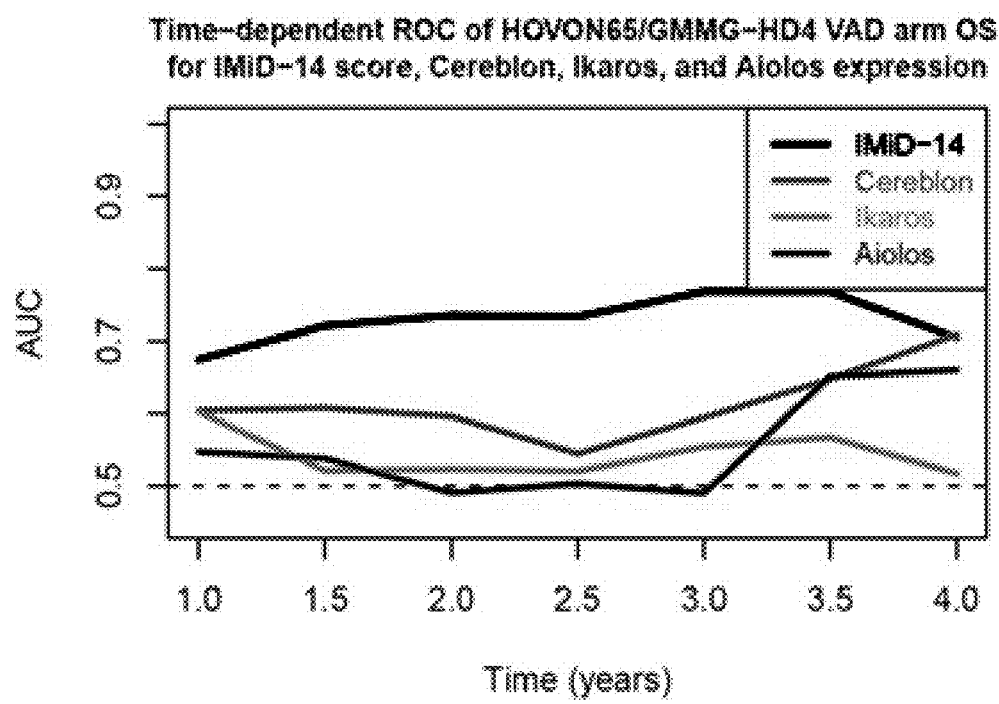
Figures 9A, 9B:
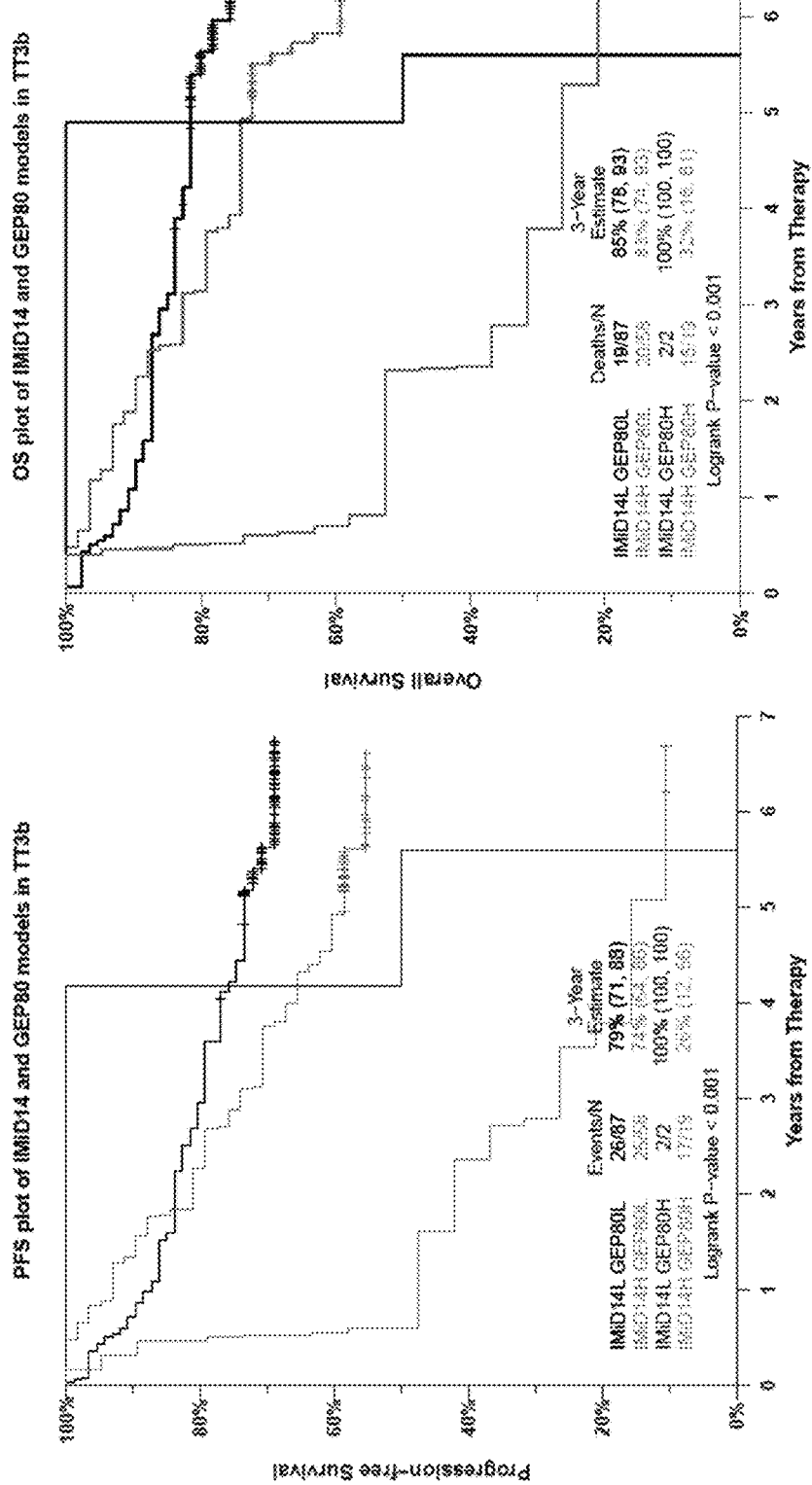
FIGS. 9A and 9B: (A) PFS plot of IMiD14 and GEP80 models in TT3b. (B) OS plot of IMiD14 and GEP80 models in TT3b.
Figures 10A, 10B:
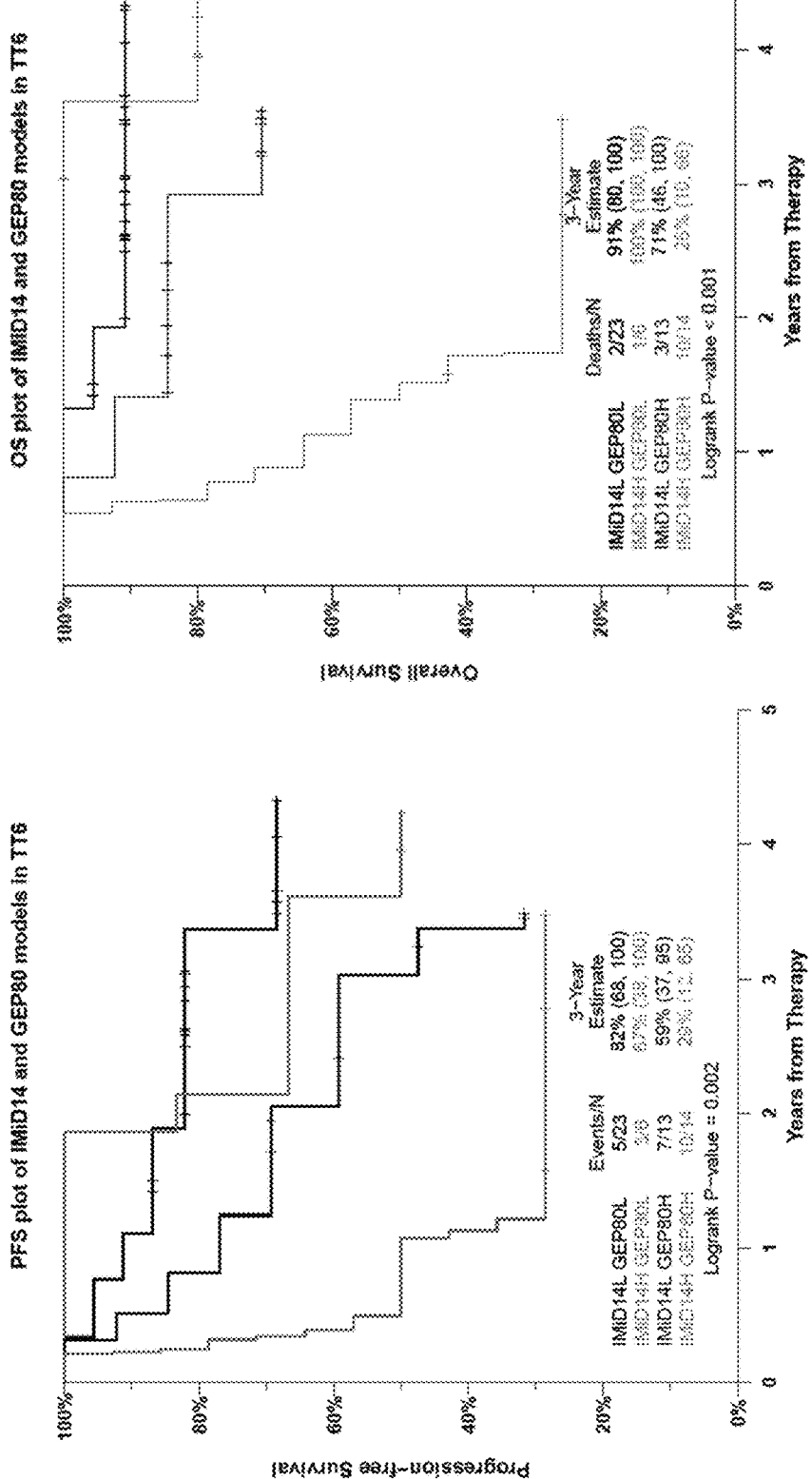
FIGS. 10A and 10B: (A) PFS plot of IMiD14 and GEP80 models in TT3a. (B) OS plot of ImiD14 and GEP80 models in TT6.

The predictive ability of IMiD-14 model was compared with other individual predictive markers, cereblon, Ikaros and Aiolos that have been previously described in literature to predict IMiDs resistance. Time-dependent ROC analysis was used for comparison and area under the curve (AUC) was used as an indication of model performance, with AUC of 0.5 indicating no predictive ability, whereas AUC of 1 representing perfect predictive ability. The IMiD-14 model showed consistently good predictive performance over the follow-up duration in both training (TT2 thalidomide arm, FIGS. 7A and 7B) and three independent test sets (TT3a, FIGS. 7C and 7D; TT3b, FIGS. 7E and 7F; and HOVON65/GMMG-HD4 VAD arm, FIGS. 7G and 7H). The IMiD-14 model outperformed expression-based cereblon, Ikaros, or Aiolos stratification approach with higher AUC in trials listed above, except by a small margin in TT3b in the first several years when comparing to Aiolos.

The following 14 genes were combined to create the IMiDs resistance score, which was the difference between the mean log 2 scale expression levels of the 4 prognosis-unfavorable genes (hazard ratio [HR]>1, XPO1, DDR2, TRAF3IP3, FAIM3) and the 10 prognosis-favorable genes (HR<1, KIAA0247, SLC39A14, PGRMC2, LAMA5, FLJ22531, ITGA6, ENO2, AMPD1, TNFRSF7, IL5RA).

| Gene | Function |
|---|---|
| UNFAVORABLE | |
| XPO1 (exportin 1) | Mediates the nuclear export of cellular proteins (cargos) bearing a leucine-rich nuclear export signal (NES) and of RNAs. Involved in the control of several cellular processes by controlling the localization of cyclin B, MPAK, and MAPKAP kinase 2. Regulates NFAT and AP-1 |
| DDR2 (discoidin domain receptor tyrosine kinase 2) | Role in the communication of cells with their microenvironment. Involved in the regulation of cell growth, differentiation, and metabolism. |
| TRAF3IP3 (TRAF3 interacting protein 3) | Encodes a protein that mediates cell growth by modulating the c-Jun N-terminal kinase signal transduction pathway. May function as an adapter molecule that regulates TRAF3-mediated JNK activation (By similarity) |
| FAIM3 (Fas apoptotic inhibitory molecule 3) | Encodes an Fc receptor for IgM. May play a role in the immune system processes. Protects cells from FAS-, TNF alpha- and FADD-induced apoptosis without increasing expression of the inhibitors of apoptosis BCL2 and BCLXL. Seems to activate an inhibitory pathway that prevents CASP8 activation following FAS stimulation, rather than blocking apoptotic signals downstream. May inhibit FAS-induced apoptosis by preventing CASP8 processing through CFLAR up-regulation |
| FAVORABLE | |
| KIAA0247 | Is a protein-coding gene. We report the isolation of a new gene termed DRAGO (drug-activated gene overexpressed, KIAA0247). This gene is activated in a p53-dependent way after DNA damage and shows potent growth-suppressive activity in vitro. DRAGO also cooperates with p53 in preventing tumor onset in vivo. |
| SLC39A14 (solute carrier family 39 (zinc transporter), member 14) | May mediate cellular uptake of nontransferrin-bound iron (By similarity). Broad-scope metal ion transporter with a preference for zinc uptake |
| PGRMC2 (progesterone receptor membrane component 2 | Heme binding and steroid binding. Receptor for steroids (Potential) |
| LAMA5 (laminin, alpha 5) | Binding to cells via a high affinity receptor, laminin is thought to mediate the attachment, migration and organization of cells into tissues during embryonic development by interacting with other extracellular matrix components |
| FLJ22531 | UNKNOWN |
| ITGA6 integrin, alpha 6 | Integrin alpha-6/beta-1 is a receptor for laminin on platelets. Integrin alpha-6/beta-4 is a receptor for laminin in epithelial cells and it plays a critical structural role in the hemidesmosome |
| ENO2 enolase 2 (gamma, neuronal) | Has neurotrophic and neuroprotective properties on a broad spectrum of central nervous system (CNS) neurons. Binds, in a calcium-dependent manner, to cultured neocortical neurons and promotes cell survival (By similarity) |
| AMPD1 adenosine monophosphate deaminase 1 | AMP deaminase plays a critical role in energy metabolism |
| TNFRSF7 Tumor Necrosis Factor Receptor Superfamily, Member 7 (CD27) | Receptor for CD70/CD27L. May play a role in survival of activated T-cells. May play a role in apoptosis through association with SIVA1 |
| IL5RA interleukin 5 receptor, alpha | This is the receptor for interleukin-5. The alpha chain binds to IL5 This protein has been found to interact with syndecan binding protein (syntenin), which is required for IL5 mediated activation of the transcription factor SOX4. |

The IMiD-14 score for IMiDs-resistance was used in combination with a proteasome inhibitor-resistance signature (GEP80, Shaugnessy et al. (2011) *Blood* 118, 3512-3524) 3-year estimates for PFS and OS for TT3a, TT3b and TT6 cohorts were determined and shown in FIGS. 8A-8B, 9A-9B, and 10A-10B, respectively. These 3-year estimates show that MM patients having an IMiD-14 and GEP80 signature indicating both IMiDs-resistance and proteasome inhibitor-resistance (IMiD-14H/GEP80H) had lower survival rates than those having an IMiD-14 and GEP80 signature indicating sensitivity to at least one treatment (IMiD-14L GEP80H or IMID-14H/GEP80L) or an IMiD-14 and GEP80 signature indicating sensitivity to both treatments (IMiD-14L/GEP80L).

Example 2

In the present study, we utilized clinical and pharmacogenomic data from MM patients who received test doses of thalidomide, lenalidomide or pomalidomide to identify genes that are altered in response to these IMiDs to build an IMiD-resistance gene signature. IMiDs and proteasome inhibitors (PI) are two classes of drugs that currently comprise the backbone of therapy for MM. By combining the IMiD-resistance signature with the PI-resistance signature (GEP80), we show that patients resistant to both drugs have the poorest survival.

GEP-based pharmacogenomics of paired CD138-purified plasma cells, obtained from patients prior to and 48 hours after administration of test doses of thalidomide (42 newly diagnosed MM), lenalidomide (18 relapsed/refractory MM), or pomalidomide (18 relapsed/refractory MM), were compared using significance analysis of microarrays (SAM). Genes that had significantly changed expression levels after 48 hours in all three IMiDs (P<0.05 by paired SAM analysis and with change in the same direction) were considered as IMiD response genes.

The total therapy (TT)2 trial thalidomide arm (newly diagnosed MM, induction T[Thalidomide]D-PACE, consolidation with tandem auto transplants and TD-PACE, maintenance with interferon and T until progression or intolerance) data were used as the training set. Baseline GEPs and PFS data were combined to build an IMiD-resistance gene signature. IMiD response genes that had P values less than 0.05 based on univariate Cox regression analysis for PFS in the training set were used to calculate the IMiD-resistance score, which was the difference between the average log 2-scale expression of prognosis-unfavorable (hazard ratio [HR]>1) and prognosis-favorable (HR<1) genes. An optimal cutoff for the IMiD-resistance score was then established with the running log-rank test, so that patients with scores higher than the cutoff were considered as IMiD-resistant.

Four independent MM data sets for which both baseline GEP of purified plasma cells and survival data were available were used as validation. All were from clinical trials in which patients received IMiD containing regimens, including TT3a (newly diagnosed MM, VTD-PACE as induction and as consolidation after tandem auto transplants, and maintenance with VTD in year 1 followed by TD in years 2 and 3), TT3b (newly diagnosed MM, induction with VTD-PACE, consolidation with tandem auto transplants and VTD-PACE, and maintenance with VR[Len]D for 3 years), TT6 (relapsed MM, induction with Mel-VTD-PACE/$1^{st}$ transplant with Mel-VRD-PACE/Mel-VTD-PACE×2/$2^{nd}$ transplant with Mel-VRD-PACE and maintenance with VRD/VMD for 3 years), and HOVON65/GMMG-HD4 trial VAD arm (newly diagnosed MM, induction with VAD, consolidation with one or two auto transplants, and maintenance with T for 2 years).

Gene expression data sets used in this study were downloaded from NIH Gene Expression Omnibus (under accession number GSE8546, GSE2658, GSE57317, and GSE19784) and EBI ArrayExpress (under accession number E-MTAB-2441 and E-TABM-1138). The MAS5 algorithm was used to preprocess and normalize Affymetrix expression data. Progression-free survival (PFS) and overall survival (OS) were estimated using Kaplan-Meier techniques and the log-rank test was used to evaluate differences between subgroups. Hazard ratios comparing risk subgroups were estimated using Cox proportional hazards models. Univariate and multivariate analyses of covariates and time-to-event outcomes were performed by Cox regression. The prognostic performances of the IMiD-14 model, cereblon, Ikaros, and Aiolos were evaluated using time-dependent receiver operating characteristics (ROC) curves for censored data. Pathway analysis was performed using the Ingenuity Pathways Analysis online tool (Ingenuity Systems, www.ingenuity.com).

Development and Validation of the IMiD-14 Model.

By applying paired SAM analysis and a 0.05 P-value cutoff, we identified 176 genes whose expression levels changed significantly 48 hours after an IMiD test dose relative to baseline (Table 3). Among 176 genes that changed significantly pre- and post-IMiD treatment, 14 had P values <0.05 based on univariate Cox regression analysis for PFS in thalidomide arm of TT2 trial (Table 1). These 14 genes were combined to create an IMiD-based risk score (IMiD-14), defined as the average log-scale differential expression of the 4 prognosis-unfavorable genes (hazard ratio [HR]>1) and the 10 prognosis-favorable (HR<1) genes. An optimal cutoff of −1.075 for the IMiD-14 score was then established with the running log-rank test, so that a patient would be classified as having IMiD-resistant disease if the score was higher than the cutoff and IMiD-sensitive disease otherwise.

The IMiD-14 risk score is calculated using the following equation:

$$\begin{aligned} IMid\text{-}14 \ \text{score} = \\ (\log_2(208775\_at) + \log_2(205168\_at) + \log_2(213888\_s\_at) + \\ \log_2(221601\_s\_at))/4 - \\ (\log_2(210744\_s\_at) + \log_2(206150\_at) + \log_2(206121\_at) + \\ \log_2(201313\_at) + \log_2(201656\_at) + \log_2(204922\_at) + \\ \log_2(210150\_s\_at) + \log_2(201701\_s\_at) + \\ \log_2(212110\_at) + \log_2(202181\_at))/10 \end{aligned}$$

The optimal cutoff for the IMiD-14 risk score is −1.075, which maximized the log-rank test statistic in the TT2 Thal training set.

In the training set TT2 Thal arm, a significant survival difference was observed between the two IMiD-14 subgroups. In the training set, patients with an IMiD-14 high score had 3-year PFS and OS of 52% and 65%, respectively, compared with 85% and 89% (PFS P<0.001, OS P<0.001) in IMiD-14 low score patients (FIGS. 1A-1B).

Next, we examined whether the IMiD-14 model had outcome discriminatory power in four independent test cohorts in which MM patients were treated with IMiDs. In TT3a, 3-year PFS and OS rates for IMiDs-14 high patients were 63% and 71%, whereas for the remainder the corresponding rates were 87% and 90% (PFS P=0.01, OS P<0.001, FIGS. 2A-2B). In TT3b, 3-year PFS and OS rates for IMiD-14 high patients were 62% and 70%, whereas for IMiD-14 low patients the corresponding rates were 80% and 85% (PFS P=0.002, OS P=0.003; FIGS. 3A-3B). In TT6, 3-year PFS and OS rates for IMiD-14 high patients were 39% and 49%, whereas for IMiD-14 low patients the corresponding rates were 74% and 83% (PFS P=0.026, OS P=0.001, FIGS. 5A-5B). The discriminatory power of the IMiD-14 model was also confirmed in the HOVON65/GMMG-HD4 trial VAD arm, with 3-year PFS and OS rates for IMiD-14 high patients of 16% and 38%, versus 54% and 82%, respectively, for the other patients (PFS P<0.001, OS P<0.001; FIGS. 11A-11B).

Pathway Analysis.

To identify pathways that were affected after IMiD intake, pathway analysis of the 176 IMiD response genes (Table 3) was performed. The top 5 most affected canonical pathways were: 1) NFAT in Regulation of the Immune Response, 2) Phospholipase C Signaling, 3) Interferon Signaling, 4) PI3K Signaling in B Lymphocytes, 5) Integrin Signaling, with details demonstrated in Tables 3 and 4. This analysis showed significant enrichment for genes of NFAT signaling pathway, which are involved in the regulation of the immune response and drug resistance.

Combination of the IMiD-14 Model and the GEP80 Model.

Patients treated with both IMiD and PI containing regimens such as the TT3a, TT3b, and TT6 trials, were divided into different risk subgroups by combining the two specialized gene signatures from the IMiD-14 and GEP80 models. Patients were divided into four subgroups: 1) IMiD-14 low and GEP80 low, 2) IMiD-14 high and GEP80 low, 3) IMiD-14 low and GEP80 high, 4) IMiD-14 high and GEP80 high.

The IMiD-14 score for IMiDs-resistance was used in combination with a proteasome inhibitor-resistance signature (GEP80, Shaugnessy et al. (2011) *Blood* 118, 3512-3524). 3-year estimates for PFS and OS for TT3a, TT3b and TT6 cohorts were determined and shown in FIGS. 8A-8B, 9A-9B, and 10A-10B, respectively. As shown, patients with both IMiD-14 and GEP80 defined high risks had the worst outcome.

Figure 12A:
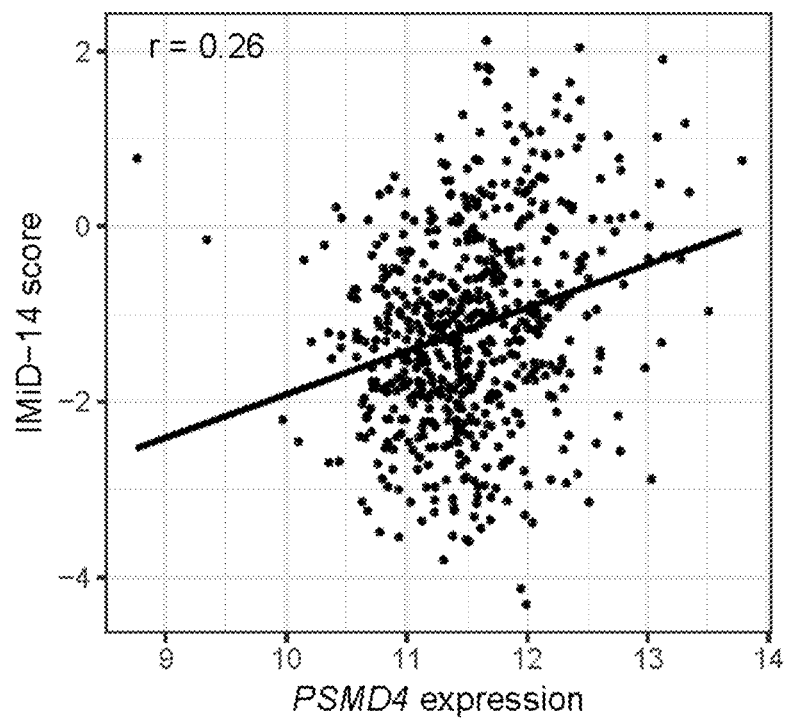
FIGS. 12A and 12B: Scatter plot with fitted regression line of (A) IMiD-14 score against PSMD4 expression, (B) GEP80 score against PSMD4 expression using combined TT2 thalidomide arm, TT3a, and TT3b GEP data. The Pearson's correlation coefficient (r) was listed on the top left corner.
Figure 12B:
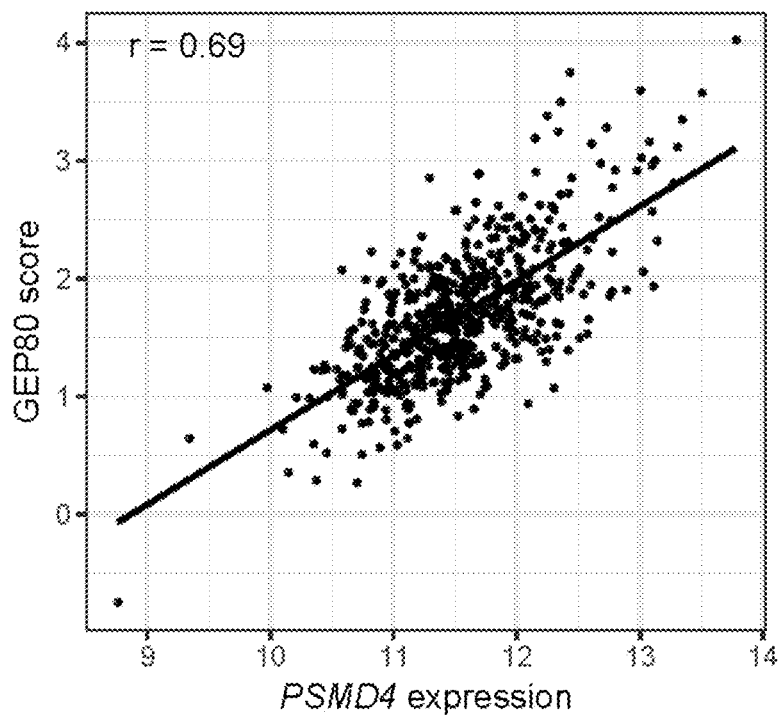
Figure 13A:
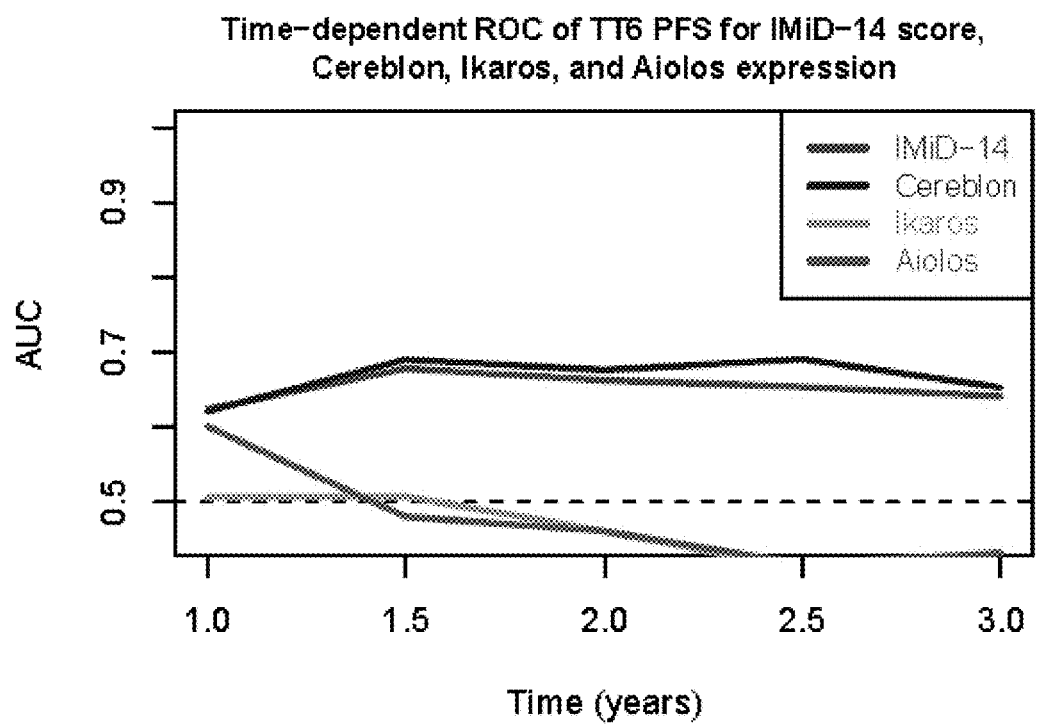
FIGS. 13A and 13B: Time-dependent ROC curves for the IMiD-14 model and IMiD resistance biomarkers. The IMiD-14 model, Cereblon, Ikaros, and Aiolos expression are shown using (A) TT6 PFS data, (B) TT6 OS data.
Figure 13B:
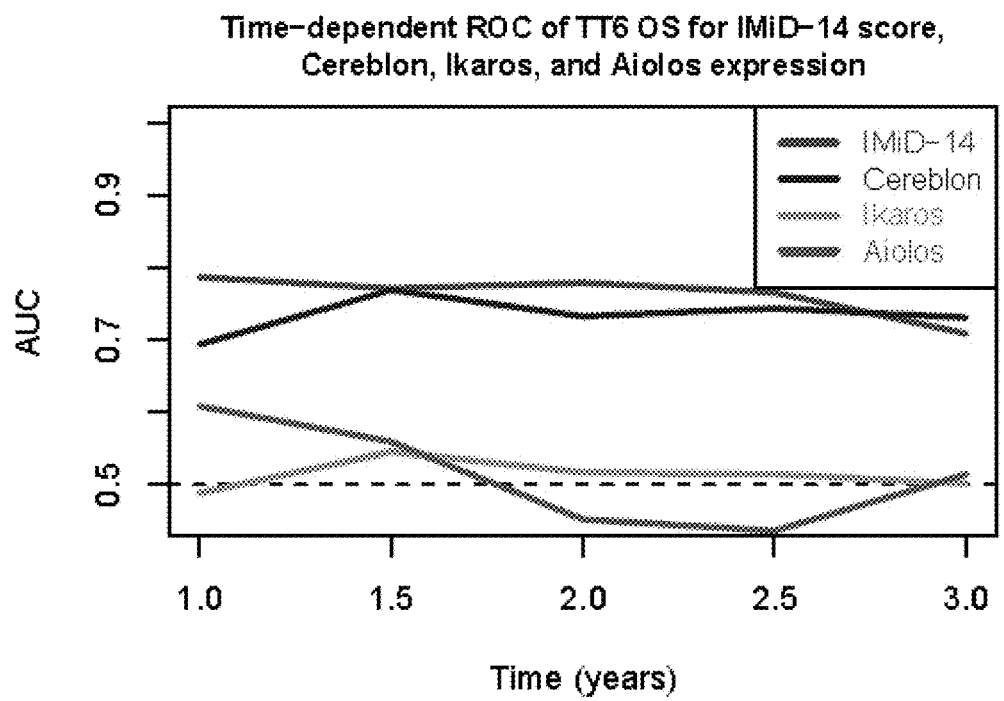

There was no gene common to both IMiD-14 model and GEP80 model. Given that three of the four prognosis-unfavorable genes in IMiD-14 model reside on chromosome 1 q, we explored whether IMiD-14 risk score is correlated with 1 q amplification. We used PSMD4 expression level as a surrogate for 1 q amplification based on our previous work showing high correlation of FISH derived 1 q copy number with PSMD4 expression levels. We found GEP80 defined risk, but not IMiD-14 defined risk, to be strongly correlated with PSMD4 expression level (FIGS. 12A-12B), hence suggesting that prognostic value of IMiD-14 model is not linked to an increase in 1 q copy number-linked PSMD4 expression.

Testing the Independent Prognostic Power of the IMiD-14 Model.

When applied to the combined training (TT2 Thal) and test (TT3a, and TT3b) data sets, in univariate analysis, several standard clinicopathologic variables, including patient's age; albumin, β2-microglobulin, creatinine, hemoglobin, and LDH levels conferred inferior PFS and OS (Table 2). High-risk designations by IMiD-14 or GEP80 models, GEP-derived TP53 deletion, PSMD4 expression level, ISS stage, and the presence of cytogenetic abnormalities also represented highly adverse features for PFS and OS in univariate analysis (Table 2). In the multivariate Cox regression analysis, IMiD-14 defined high risk, along with ISS stage III, high LDH, cytogenetic abnormalities, and GEP80 defined high risk predicted inferior PFS and OS (Table 2).

Comparison of the Prognostic Performance of the IMiD-14 Model and IMiD-Related Biomarkers.

We then compared the prognostic performance of the IMiD-14 model with the IMiD-related biomarkers cereblon, ikaros and Aiolos, which have previously been described to predict IMiD resistance. Time-dependent ROC analysis for censored data and area under the curve (AUC) was used as an indication of model performance, with AUC of 0.5 indicating no predictive ability, whereas AUC of 1 representing perfect predictive ability. The IMiD-14 model showed consistently good prognostic performance over the follow-up duration in both the training (TT2 Thal arm) and four independent test sets (TT3a, TT3b, HOVON65/GMMG-HD4 VAD arm, and TT6; FIGS. 7A-7H, FIGS. 13A-13B) with an AUC of approximately 0.7. The IMiD-14 model outperformed stratification based on expression of cereblon, Ikaros, or Aiolos, which yielded higher AUCs. The one exception was Aiolos expression in the first several years of TT3b.

In this study, a signature of fourteen genes created from IMiD-specific GEP pharmacogenomics data was associated with clinical outcome after IMiD-based treatment in MM. The IMiD-14 model was cross-validated in four independent GEP datasets from clinical trials employing regimens that included IMiDs. In each of these studies, patients with high IMiD-14 scores exhibited poor PFS and OS compared with patients who had low IMiD-14 scores. Other commonly used molecular signatures such as GEP70 and EMC92 have been used to stratify MM patients into different risk categories, and can distinguish 10-30% of patients at high risk of relapse. However, the focus of these signatures differs from the IMiD-14 model in that they are based on outcomes from more than one chemotherapeutic regimen rather than specific to a class of drugs. The IMiD-14 model, on the other hand, is derived from a set of fourteen survival discriminatory genes that are altered specifically after short-term exposure to single agent thalidomide, lenalidomide, or pomalidomide, thereby suggesting that these genes represent specific tumor or tumor microenvironment responses to the IMiD class. In both training and testing datasets, patients with high IMiD-14 scores, who were theoretically resistant to IMiDs, showed PFS and OS inferior to that of patients with low IMiD-14 scores after IMiD inclusive therapies.

In the real-world scenario, patients with MM are often treated with therapy consisting of an IMiD or a PI or combinations of these drugs when appropriate. We combined the IMiD-14 model with a PI-related prognostic model derived from bortezomib response genes, the GEP80 signature. Combination of these two drug-specific gene signatures stratified patients into four risk subgroups based on IMiD and PI resistance and sensitivity. For patients treated with both an IMiD and PI, the subgroup that had high scores for both IMiD-14 and GEP80 showed the lowest rate of OS and PFS, while the other three subgroups did not have clear separation across all tested datasets. In the multivariate Cox regression analysis, IMiD-14 defined high risk was an independent adverse predictor for PFS and OS, in addition to GEP80 defined high risk and ISS stage III. Hence, the IMiD-14 model complements the GEP80 model as a valuable prognostic tool in MM patients treated with IMiDs and PI. For patients predicted to be resistant to both drugs, it might be worthwhile to consider adding new classes of drugs or later generation IMiDs or PIs.

Furthermore, in this study, the IMiD-14 model outperformed other previously described individual IMiD-resistance biomarkers, such as cereblon, ikaros and Aiolos in predicting survival outcomes. The canonical pathway analysis of 176 IMiD response genes showed enrichment for NFAT (Nuclear Factor of Activated T cell) regulated immune response pathway, and other pathways involved in phosphate C, interferon, PI3kinase and integrin signaling NFAT proteins are transcriptional activators of interleukin-2, a key regulator of T cell immune response. IMiDs mediate their function, in part, via nuclear translocation of NFAT2 and AP-1 via activation of PI3kinase signaling, resulting in IL-2 secretion and T cell proliferation. Other studies suggest that overexpression of the exportin XPO1/CRM1 can mediate nuclear export of NFAT resulting in termination of its action. In addition to NFAT, XPO1 can mediate nuclear export of other key cargo proteins including cyclin B, MAPK, and AP-1. Interestingly, XPO1 was the top-ranking gene in the IMiD-14 model that was overexpressed and associated with poor prognosis. High expression of XPO1 has been associated with poor survival in other cancers as well. Selinexor is a XPO1 antagonist in clinical development, being evaluated in multiple clinical trials in patients with relapsed and/or refractory multiple myeloma. Emerging data indicate that selinexor is a promising agent for patients with penta-refractory disease (resistant to daratumumab, carfilzomib, bortezomib, pomalidomide and lenalidomide) and several studies are evaluating selinexor in combination with existing therapies across the broader population in multiple myeloma.

Other genes in the IMiD-14 model have been implicated in functions involving cell growth, migration, differentiation, and metabolism. The gene worthy of note in the prognosis favorable group is TNFRSF7. The protein encoded by this gene CD27 is a costimulatory receptor that is expressed on the surface of T, B and NK cell, providing a target for enhancing NK-mediated tumor clearance while generating adaptive immune response by IMiDs. Other genes of interest include LAMA5 and ITGA6, which play a role in cell-matrix interactions and mediate cell adhesion to endothelium. The treatment with IMiD has shown to decrease expression of integrin subunits and/or integrin receptors.

In conclusion, these data demonstrate that different risk groups can be identified using the IMiD-14 model that are associated with significantly different outcomes in MM patients receiving polychemotherapy that includes IMiDs. The IMiD-14 model adds new knowledge to the field, and we are further validating this gene signature in prospective clinical studies. The addition of the IMiD-14 model to traditionally used clinical and pathological factors could provide valuable information for determining which patients might benefit from IMiDs, so that patients predicted to derive less clinical benefit from IMiDs could be offered alternative treatment regimens including new classes such as monoclonal antibodies, other immunotherapies, and epigenetic therapies. Unlike traditional MM gene signatures which predict the overall effect of a certain combination therapy, the drug specific gene signatures derived from pharmacogenomics studies, such as the IMiD-14 and GEP80 models, are useful complementary tools in the era of personalized medicine.

While there are shown and described particular embodiments of the invention, it is to be understood that the invention is not limited thereto but may be otherwise variously embodied and practiced within the scope of the following claims. Since numerous modifications and alternative embodiments of the present invention will be readily apparent to those skilled in the art, this description is to be construed as illustrative only and is for the purpose of teaching those skilled in the art the best mode for carrying out the present invention. Accordingly, all suitable modifications and equivalents may be considered to fall within the scope of the following claims.

TABLE 1

List of 14 genes in the IMiD-14 model that are altered 48 hours after IMiD test-dosing and linked to PFS in TT2 thalidomide arm

| Probeset | Gene symbol | Chromosomal location | Expression 48 hr after IMiDs | P for PFS | PFS HR |
|---|---|---|---|---|---|
| Prognosis-unfavorable genes | | | | | |
| 208775_at | XPO1 | chr2p16 | increase | 0.005 | 1.83 |
| 205168_at | DDR2 | chr1q12-q23 | increase | 0.016 | 1.23 |
| 213888_s_at | TRAF3IP3 | chr1q32.3-q41 | increase | 0.011 | 1.21 |
| 221601_s_at | FAIM3 | chr1q32.1 | decrease | 0.030 | 1.13 |
| Prognosis-favorable genes | | | | | |
| 210744_s_at | IL5RA | chr3p26-p24 | decrease | 0.033 | 0.90 |
| 206150_at | TNFRSF7 | chr12p13 | decrease | 0.020 | 0.87 |
| 206121_at | AMPD1 | chr1p13 | decrease | 0.031 | 0.85 |
| 201313_at | ENO2 | chr12p13 | decrease | 0.001 | 0.84 |
| 201656_at | ITGA6 | chr2q31.1 | decrease | 0.005 | 0.82 |
| 204922_at | FLJ22531 | chr11q13.1 | decrease | 0.004 | 0.78 |
| 210150_s_at | LAMA5 | chr20q13.2-q13.3 | decrease | 0.014 | 0.74 |
| 201701_s_at | PGRMC2 | chr4q26 | decrease | 0.023 | 0.68 |
| 212110_at | SLC39A14 | chr8p21.3 | increase | 0.005 | 0.68 |
| 202181_at | KIAA0247 | chr14q24.1 | increase | 0.042 | 0.66 |

Genes are ordered by descending hazard ratio (HR)

TABLE 2

Univariate and multivariate Cox regression analysis of PFS and OS for combined training (TT2 Thal arm, n = 166) and test sets (TT3A, n = 266 and TT3B, n = 160)

| Variable | n/N (%) | PFS HR (95% CI) | Wald P* | OS HR (95% CI) | Wald P* |
|---|---|---|---|---|---|
| Univariate Cox regression analysis† | | | | | |
| Age ≥65 y | 151/592 (26) | 1.28 (1.00-1.64) | 0.048 | 1.50 (1.14-1.98) | 0.004 |
| Albumin level <3.5 g/dL | 172/592 (29) | 1.35 (1.07-1.72) | 0.013 | 1.46 (1.11-1.91) | 0.006 |
| B2M level ≥3.5 mg/L | 284/592 (48) | 1.61 (1.28-2.01) | <0.001 | 1.94 (1.50-2.51) | <0.001 |
| ISS Stage III | 141/592 (24) | 2.20 (1.73-2.80) | <0.001 | 2.47 (1.90-3.23) | <0.001 |
| Creatinine level ≥2.0 mg/dL | 48/592 (8) | 2.20 (1.57-3.10) | <0.001 | 2.03 (1.38-2.97) | <0.001 |
| CRP level ≥8 mg/L | 207/592 (35) | 1.12 (0.89-1.41) | 0.338 | 1.36 (1.05-1.76) | 0.019 |
| Hb level <10 g/dL | 181/592 (31) | 1.49 (1.18-1.88) | 0.001 | 1.49 (1.15-1.94) | 0.003 |

TABLE 2-continued

Univariate and multivariate Cox regression analysis of PFS and OS for combined training (TT2 Thal arm, n = 166) and test sets (TT3A, n = 266 and TT3B, n = 160)

| Variable | n/N (%) | PFS HR (95% CI) | Wald P* | OS HR (95% CI) | Wald P* |
|---|---|---|---|---|---|
| LDH level ≥190 U/L | 171/592 (29) | 1.75 (1.39-2.21) | <0.001 | 2.10 (1.62-2.73) | <0.001 |
| Cytogenetic Abnormalities | 207/592 (35) | 1.73 (1.38-2.16) | <0.001 | 2.15 (1.67-2.78) | <0.001 |
| GEP TP53 deletion | 61/592 (10) | 1.44 (1.02-2.03) | 0.037 | 1.93 (1.35-2.76) | <0.001 |
| GEP80 high risk | 45/592 (8) | 3.53 (2.51-4.98) | <0.001 | 4.22 (2.95-6.04) | <0.001 |
| PSMD4 level tertile 2 or 3 | 394/592 (67) | 1.58 (1.23-2.03) | <0.001 | 1.83 (1.36-2.46) | <0.001 |
| IMiD-14 high risk | 262/592 (44) | 1.96 (1.57-2.45) | <0.001 | 2.30 (1.78-2.99) | <0.001 |
| Multivariate Cox regression analysis‡ | | | | | |
| ISS Stage III | 141/592 (24) | 1.76 (1.37-2.25) | <0.001 | 1.88 (1.42-2.49) | <0.001 |
| LDH level ≥190 U/L | 171/592 (29) | 1.35 (1.05-1.73) | 0.018 | 1.49 (1.12-1.97) | 0.006 |
| Cytogenetic Abnormalities | 207/592 (35) | 1.32 (1.04-1.68) | 0.023 | 1.52 (1.16-2.01) | 0.003 |
| GEP TP53 deletion | 61/592 (10) | — | — | 1.80 (1.25-2.60) | 0.002 |
| GEP80 high risk | 45/592 (8) | 2.00 (1.37-2.92) | <0.001 | 1.99 (1.33-2.98) | 0.001 |
| IMiD-14 high risk | 262/592 (44) | 1.67 (1.32-2.11) | <0.001 | 1.93 (1.47-2.54) | <0.001 |

95% CI indicates 95% confidence interval;
B2M, β2-microglobulin;
ISS, International Staging System;
CRP, C-reactive protein; and
Hb, hemoglobin.
*Determined with Wald chi-square test in Cox regression.
†All univariate P values were reported regardless of significance. Variables with univariate P <0.05 were considered for selection in the multivariate analysis.
‡Multivariate model uses backward selection with entry level 0.05 and variable remains if meets the 0.05 level.

TABLE 3

List of 176 genes whose expression levels changed significantly 48 hours after an IMiD test dose relative to baseline

| Gene symbol | Chromosomal location | Expression 48 hr after IMiDs |
|---|---|---|
| ACVR1 | chr2q24.1 | increase |
| AGPAT7 | chr15q14 | increase |
| AKAP12 | chr6q25.1 | increase |
| AMPD1 | chr1p13.2 | decrease |
| ANKRD15 | chr9p24.3 | increase |
| ANXA4 | chr2p14 | increase |
| ANXA6 | chr5q33.1 | increase |
| AQP3 | chr9p13.3 | decrease |
| ARF3 | chr12q13.12 | increase |
| ARHGEF5 | chr7q35 | increase |
| ARL6IP5 | chr3p14.1 | increase |
| ATP10D | chr4p12 | increase |
| ATP2A3 | chr17p13.2 | decrease |
| ATP6V1A | chr3q13.2 | increase |
| AZIN1 | chr8q22.3 | decrease |
| B4GALT3 | chr1q23.3 | decrease |
| BAZ1A | chr14q13.2 | increase |
| BLVRB | chr19q13.2 | increase |
| BMPR2 | chr2q33.1 | increase |
| BST2 | chr19p13.11 | increase |
| BTBD3 | chr20p12.2 | decrease |
| C10orf10 | chr10q11.21 | increase |
| C22orf5 | chr22q13.1 | decrease |
| C5orf21 | chr5q15 | decrease |
| CA11 | chr19q13.33 | increase |
| CAMSAP1L1 | chr1q32.1 | increase |
| CAPN2 | chr1q41 | increase |
| CASP1 | chr11q22.3 | increase |
| CASP4 | chr11q22.3 | increase |
| CAV2 | chr7q31.2 | increase |
| CCL3 | chr17 | decrease |
| CCNC | chr6q16.3 | increase |
| CCND3 | chr6p21.1 | increase |
| CCNG2 | chr4q21.1 | decrease |
| CD164 | chr6q21 | increase |
| CD97 | chr19p13.12 | increase |
| CEACAM1 | chr19q13.2 | increase |
| CFB | chr6p21.32 | increase |
| CIB1 | chr15q26.1 | increase |
| CR2 | chr1q32.2 | decrease |
| CRTAP | chr3p22.3 | increase |
| CRYZ | chr1p31.1 | increase |
| CSF2RB | chr22q12.3 | decrease |
| CSNK1E | chr22q13.1 | decrease |
| CTNND1 | chr11q12.1 | increase |
| CTSZ | chr20q13.32 | increase |
| CYFIP1 | chr15q11.2 | increase |
| DDIT4 | chr10q22.1 | increase |
| DDR2 | chr1q23.3 | increase |
| DEK | chr6p22.3 | increase |
| DKFZP564O0823 | chr4q13.3 | decrease |
| DKK1 | chr10q21.1 | increase |
| DNAJA1 | chr9p13.3 | increase |
| DOCK4 | chr7q31.1 | increase |
| DPYD | chr1p21.3 | increase |
| DUSP1 | chr5q35.1 | decrease |
| DUSP3 | chr17q21.31 | increase |
| E2F3 | chr6p22.3 | increase |
| ENO2 | chr12p13.31 | decrease |
| ENTH | chr5q33.3 | increase |
| F12 | chr5q35.3 | decrease |
| FAIM3 | chr1q32.1 | decrease |
| FAM119B | chr12q14.1 | increase |
| FCGR2A | chr1q23.3 | increase |
| FCGR2B | chr1q23.3 | increase |
| FCGR2C | chr1q23.3 | increase |

TABLE 3-continued

List of 176 genes whose expression levels changed significantly 48 hours after an IMiD test dose relative to baseline

| Gene symbol | Chromosomal location | Expression 48 hr after IMiDs |
| --- | --- | --- |
| FER1L3 | chr10q23.33 | increase |
| FKBP5 | chr6p21.31 | increase |
| FLJ22531 | chr11q13.1 | decrease |
| FZD2 | chr17q21.31 | decrease |
| GALNAC4S-6ST | chr10q26.13 | increase |
| GAS6 | chr13q34 | increase |
| GORASP1 | chr3p22.2 | increase |
| GPNMB | chr7p15.3 | decrease |
| GPX1 | chr3p21.31 | increase |
| GRM8 | chr7q31.33 | increase |
| GSTO1 | chr10q25.1 | increase |
| HCLS1 | chr3q13.33 | decrease |
| HLA-DOB | chr6p21.32 | decrease |
| HLA-F | chr6p22.1 | increase |
| HOMER3 | chr19p13.11 | decrease |
| ID2 | chr2p25.1 | increase |
| IDH1 | chr2q33.3 | increase |
| IFI27 | chr14q32.13 | increase |
| IFI30 | chr19p13.11 | increase |
| IFIT1 | chr10q23.31 | increase |
| IFIT3 | chr10q23.31 | increase |
| IFITM2 | chr11p15.5 | increase |
| IFITM3 | chr11p15.5 | increase |
| IFNAR2 | chr21q22.11 | decrease |
| IGSF4 | chr11q23.2 | decrease |
| IL13RA1 | chrXq24 | increase |
| IL5RA | chr3p26.3 | decrease |
| IL6ST | chr17p12 | increase |
| ITGA6 | chr2q31.1 | decrease |
| ITGA8 | chr10p13 | decrease |
| ITGB1 | chr10p11.22 | increase |
| ITGB7 | chr12q13.13 | increase |
| ITPR3 | chr6p21.31 | decrease |
| JUN | chr1p32.1 | decrease |
| KCNA3 | chr1p13.3 | decrease |
| KIAA0247 | chr14q24.1 | increase |
| LAMA5 | chr20q13.33 | decrease |
| LAMP3 | chr3q27.1 | increase |
| LGALS3BP | chr17q25.3 | increase |
| LY6E | chr8q24.3 | increase |
| LYN | chr8q12.1 | increase |
| MACF1 | chr1p34.3 | increase |
| MAP2K1 | chr15q22.31 | increase |
| MCFD2 | chr2p21 | increase |
| MUC1 | chr1q22 | increase |
| MX2 | chr21q22.3 | increase |
| MYO1B | chr2q32.3 | increase |
| NAT1 | chr8p22 | increase |
| NCF4 | chr22q12.3 | increase |
| NFE2L1 | chr17q21.32 | decrease |
| NME3 | chr16p13.3 | decrease |
| NPM3 | chr10q24.32 | decrease |
| P2RX5 | chr17p13.3 | decrease |
| P2RY6 | chr11q13.4 | increase |
| PBXIP1 | chr1q21.3 | increase |
| PCTK3 | chr1q32.1 | increase |
| PEA15 | chr1q23.2 | increase |
| PFTK1 | chr7q21.13 | increase |
| PGRMC2 | chr4q28.2 | decrease |
| PHF15 | chr5q31.1 | increase |
| PLA2G4C | chr19q13.32 | increase |
| PLP2 | chrXp11.23 | decrease |
| PLSCR1 | chr3q24 | increase |
| PMS2L1 | chr7q11.23 | decrease |
| PON2 | chr7q21.3 | increase |
| PPIC | chr5q23.2 | increase |
| PPP1R16B | chr20q11.23 | decrease |
| PPP2R4 | chr9q34.11 | increase |
| PRDX6 | chr1q25.1 | increase |
| PTPN12 | chr7q11.23 | increase |
| QPRT | chr16p11.2 | increase |
| RAB13 | chr1q21.3 | increase |
| RAB30 | chr11q14.1 | decrease |
| RABGAP1L | chr1q25.1 | increase |
| RAC1 | chr7p22.1 | increase |
| RARRES3 | chr11q12.3 | increase |
| RASGRP1 | chr15q14 | decrease |
| RGS1 | chr1q31.2 | decrease |
| RNGTT | chr6q15 | decrease |
| RNPEP | chr1q32.1 | increase |
| RRAS | chr19q13.33 | increase |
| SAMHD1 | chr20q11.23 | increase |
| SCAMP5 | chr15q24.1 | decrease |
| SECTM1 | chr17q25.3 | increase |
| SERPINB1 | chr6p25.2 | increase |
| SERPINH1 | chr11q13.5 | increase |
| SERPINI1 | chr3q26.1 | increase |
| SIP1 | chr14q21.1 | decrease |
| SLA | chr8q24.22 | increase |
| SLC39A14 | chr8p21.3 | increase |
| SMA3 | chr5q13.2 | decrease |
| SPR | chr2p13.2 | increase |
| SSBP2 | chr5q14.1 | increase |
| STARD5 | chr15q25.1 | increase |
| STK3 | chr8q22.2 | increase |
| SYNE2 | chr14q23.2 | decrease |
| SYPL1 | chr7q22.2 | decrease |
| TGFBR2 | chr3p24.1 | increase |
| TMED1 | chr19p13.2 | increase |
| TMED5 | chr1p22.1 | decrease |
| TMEFF1 | chr9q31.1 | decrease |
| TNFRSF7 | chr12p13.31 | decrease |
| TNFSF10 | chr3q26.31 | increase |
| TRAF3IP3 | chr1q32.2 | increase |
| TRIP10 | chr19p13.3 | increase |
| TSPAN7 | chrXp11.4 | increase |
| UNC13B | chr9p13.3 | increase |
| WASF1 | chr6q21 | increase |
| XPO1 | chr2p15 | increase |
| ZNFN1A1 | chr7p12.2 | increase |

TABLE 4

The top 5 most affected canonical pathways after test-dosing IMiD intake

| Canonical pathway | B-H p-value* | Genes overlapped with the listed pathway |
| --- | --- | --- |
| Role of NFAT in Regulation of the Immune Response | 4.96E−04 | CSNK1E, FCGR2C, JUN, FCGR2A, RRAS, ITPR3, LYN, HLA-DOB, XPO1, FCGR2B, MAP2K1 |
| Phospholipase C Signaling | 2.95E−03 | ITGB1, FCGR2C, ARHGEF5, RRAS, ITPR3, PLA2G4C, LYN, RAC1, FCGR2B, MAP2K1 |
| Interferon Signaling | 3.14E−03 | IFITM3, IFIT3, IFIT1, IFNAR2, IFITM2 |

TABLE 4-continued

The top 5 most affected canonical pathways after test-dosing IMiD intake

| Canonical pathway | B-H p-value* | Genes overlapped with the listed pathway |
|---|---|---|
| PI3K Signaling in B Lymphocytes | 3.14E−03 | JUN, RRAS, ITPR3, LYN, RAC1, FCGR2B, MAP2K1, CR2 |
| Integrin Signaling | 3.86E−03 | ITGB1, TSPAN7, RRAS, ARF3, ITGA8, RAC1, ITGA6, CAPN2, MAP2K1, ITGB7 |

*Benjamini-Hochberg adjusted p-value.

That which is claimed is:

1. A method of treating a human subject having multiple myeloma (MM), comprising:
   obtaining a sample containing paired CD138-purified plasma cells from the subject;
   measuring an mRNA level in the sample of each of the prognosis-favorable genes for IMiDs response: KIAA0247, SLC39A14, PGRMC2, LAMA5, FLJ22531, ITGA6, ENO2, AMPD1, TNFRSF7 and IL5RA;
   measuring an mRNA level in the sample of each of the prognosis-unfavorable genes for IMiDs response: XPO1, DDR1, TRAFIP3 and FAIM3;
   normalizing the mRNA level of the prognosis-favorable genes for IMiDs response to obtain a normalized mRNA level for the prognosis-favorable genes for IMiDs response and normalizing the mRNA level of the prognosis-unfavorable genes IMiDs response to obtain a normalized mRNA level for the prognosis-unfavorable genes IMiDs response;
   identifying a difference between the normalized mRNA level for the prognosis-favorable genes for IMiDs response and the normalized mRNA level for the prognosis-unfavorable genes IMiDs response to provide a gene expression profile (GEP) or signature; and
   comparing the gene expression profile or signature to a pre-defined threshold value, wherein the gene expression profile or signature that exceeds the threshold value identifies the subject as having an increased risk of developing IMiDs resistance; and
   treating the subject identified as having an increased risk of developing IMiDs resistance with a non-IMiD therapy selected from the group consisting of:
   a) bortezomib-dexamethasone (VD),
   b) bortezomib-cyclophosphamide-dexamethasone with daratumumab (CyBorD-Dara),
   c) bortezomib-cyclophosphamide-dexamethasone without daratumumab (CyBorD),
   d) carfilzomib-cytoxan-dexamethasone (Car-Cy-Dex),
   e) bortezomib-melphalan-prednisone with daratumumab (VMP-Dara,
   f) bortezomib-melphalan-prednisone without daratumumab (VMP),
   g) bortezomib-dexamethasone-cisplatin-Adriamycin-cyclophosphamide-etoposide (VD-PACE), and
   h) any combination of (a)-(g).

2. The method of claim 1, wherein the mRNA level of prognosis-favorable genes for IMiDs response and the mRNA level of prognosis-unfavorable genes for IMiDs response is normalized by the MAS5 method.

3. The method of claim 1, wherein the pre-defined threshold value is −1.075.

4. The method of claim 1, wherein the gene expression profile or signature is calculated using the following equation:

$$GEP = [(\log_2(205168\_at) + \log_2(208775\_at) +$$
$$\log_2(213888\_s\_at) + \log_2(221601\_s\_at))/4] -$$
$$[(\log_2(201313\_at) + \log_2(201656\_at) + \log_2(201701\_s\_at) +$$
$$\log_2(202181\_at) + \log_2(204922\_at) + \log_2(206121\_at) +$$
$$\log_2(206150\_at) + \log_2(210150\_s\_at) +$$
$$\log_2(210744\_s\_at) + \log_8(212110\_at))/10].$$

5. The method of claim 1, wherein the subject has relapsed/refractory MM.

6. The method of claim 1, wherein the subject does not have relapsed/refractory MM.

7. The method of claim 1, wherein the subject is undergoing and/or has undergone a hematopoietic stem cell transplant.

8. The method of claim 1, wherein the subject is not undergoing and/or has not undergone a hematopoietic stem cell transplant.

* * * * *

UNITED STATES PATENT AND TRADEMARK OFFICE
CERTIFICATE OF CORRECTION

PATENT NO.         : 10,697,024 B2                                           Page 1 of 1
APPLICATION NO.    : 15/821286
DATED              : June 30, 2020
INVENTOR(S)        : Usmani et al.

It is certified that error appears in the above-identified patent and that said Letters Patent is hereby corrected as shown below:

In the Specification

Column 12, Line 17: Please correct "$\log_s(212110\_at)$" to read -- $\log_2(212110\_at)$ --

Column 15, Line 58: Please correct "$\log_s(212110\_at)$" to read -- $\log_2(212110\_at)$ --

Column 20, Line 44: Please correct "$\log_s(212110\_at)$" to read -- $\log_2(212110\_at)$ --

In the Claims

Column 30, Line 17, Claim 1: Please correct "-Adriamycin-cv-" to read -- -Adriamycin-cy- --

Column 30, Line 39, Claim 4: Please correct "$\log_s(212110\_at)$" to read -- $\log_2(212110\_at)$ --

Signed and Sealed this
Twelfth Day of January, 2021

Andrei Iancu
*Director of the United States Patent and Trademark Office*